United States Patent
Pahan

(10) Patent No.: US 11,034,758 B2
(45) Date of Patent: Jun. 15, 2021

(54) COMPOSITIONS AND METHODS FOR TREATING PARKINSON'S DISEASE

(71) Applicant: Rush University Medical Center, Chicago, IL (US)

(72) Inventor: Kalipada Pahan, Skokie, IL (US)

(73) Assignee: Rush University Medical Center, Chicago, IL (US)

( * ) Notice: Subject to any disclaimer, the term of this patent is extended or adjusted under 35 U.S.C. 154(b) by 0 days.

(21) Appl. No.: 16/083,655

(22) PCT Filed: Mar. 9, 2017

(86) PCT No.: PCT/US2017/021541
§ 371 (c)(1),
(2) Date: Sep. 10, 2018

(87) PCT Pub. No.: WO2017/156248
PCT Pub. Date: Sep. 14, 2017

(65) Prior Publication Data
US 2019/0071494 A1 Mar. 7, 2019

Related U.S. Application Data

(60) Provisional application No. 62/307,072, filed on Mar. 11, 2016.

(51) Int. Cl.
*C07K 16/24* (2006.01)
*A61P 25/16* (2006.01)
*A61K 39/00* (2006.01)
*C12Q 1/6883* (2018.01)

(52) U.S. Cl.
CPC .............. *C07K 16/24* (2013.01); *A61P 25/16* (2018.01); *C12Q 1/6883* (2013.01); *A61K 2039/505* (2013.01); *A61K 2039/507* (2013.01); *C07K 2317/76* (2013.01); *C12Q 2600/158* (2013.01)

(58) Field of Classification Search
CPC ..... C07K 16/24; C07K 2317/76; A61P 25/16; A61P 25/28; A61K 2039/505; A61K 2039/507; A61K 39/3955
See application file for complete search history.

(56) References Cited

U.S. PATENT DOCUMENTS

| | | |
|---|---|---|
| 2008/0287363 A1 | 11/2008 | Proudfoot et al. |
| 2010/0227805 A1 | 9/2010 | Karin et al. |
| 2014/0357656 A1 | 12/2014 | Zhang et al. |

FOREIGN PATENT DOCUMENTS

| | | |
|---|---|---|
| WO | WO 2002/064612 A2 | 8/2002 |
| WO | WO 2011/094535 A2 | 8/2011 |
| WO | WO 2012/009544 A2 | 1/2012 |
| WO | WO 2014/037952 A1 | 3/2014 |

OTHER PUBLICATIONS

Gibrat C et al. J. Neurochem. 109, 1469-1482. (Year: 2009).*
Liu et al. Int. J. Clin. Exp. Pathol. 7(12), 8342-8355. (Year: 2014).*
Chou et al. J. Neurosci. 28(13), 3277-3290. (Year: 2008).*
Villeda et al. Nature, 477, 90-96. (Year: 2011).*
Kalkonde et al. Brain Res. 1128, 1-11. (Year: 2007).*
Chandra G et al. Neutralization of RANTES and eotaxin prevents the loss of dopaminergic neurons in a mouse model of Parkinson disease. J. Biol. Chem. 291 (29), 15267-15281. (Year: 2016).*
Dorr, Patrick et al.; "Maraviroc (UK-427,857), a Potent, Orally Bioavailable, and Selective Small-Molecule Inhibitor of Chemokine Receptor CCR5 with Broad-Spectrum Anti-Human Immunodeficiency Virus Type 1 Activity"; Antimicrobial Agents and Chemotherapy, vol. 49, No. 11; Nov. 2005; pp. 4721-4732.
Appay, V. et al.; "RANTES: a versatile and controversial chemokine"; Trends in Immunology, vol. 22; Feb. 2001; pp. 83-87.
Benner, E. J. et al.; "Therapeutic immunization protects dopaminergic neurons in a mouse model of Parkinson's disease"; Proceedings of the National Academy of Sciences of the United States of America, vol. 101, Jun. 22, 2004; pp. 9435-9440.
Benner, E. J. et al.; "Nitrated alpha-synuclein immunity accelerates degeneration of nigral dopaminergic neurons"; PLoS One, vol. 3, Issue 1; Jan. 2008; e1376; 20 pages.
Brahmachari, S. et al.; "Gender-specific expression of beta1 integrin of VLA-4 in myelin basic protein-primed T cells: implications for gender bias in multiple sclerosis" Journal of Immunology, vol. 184; May 2010; pp. 6103-6113.
Brahmachari, S. et al.; "Sodium benzoate, a metabolite of cinnamon and a food additive, reduces microglial and astroglial inflammatory responses"; Journal of Immunology, vol. 183; Oct. 2009; pp. 5917-5927.
Brochard, V. et al.; "Infiltration of CD4+ lymphocytes into the brain contributes to neurodegeneration in a mouse model of Parkinson disease"; Journal of Clinical Investigation, vol. 119; Jan. 2009; pp. 182-192.
Chabot, S. et al.; "Cytokine production consequent to T cell—microglia interaction: the PMA/IFN gamma-treated U937 cells display similarities to human microglia"; Journal of Neuroscience Methods, vol. 105; Feb. 15, 2001; pp. 111-120.
Cunningham, C. et al.; "Systemic inflammation induces acute behavioral and cognitive changes and accelerates neurodegenerative disease"; Biological Psychiatry, vol. 65; Feb. 15, 2009; pp. 304-312.
Dasgupta, S. et al.; "Myelin basic protein-primed T cells induce nitric oxide synthase in microglial cells. Implications for multiple sclerosis"; Journal of Biological Chemistry, vol. 277; Aug. 2002; pp. 39327-39333.

(Continued)

*Primary Examiner* — Kimberly Ballard
(74) *Attorney, Agent, or Firm* — Barnes & Thornburg LLP

(57) ABSTRACT

A composition and a method for the treatment of a neurodegenerative disorder is provided. The composition includes an inhibitor of RANTES and/or an inhibitor of eotaxin. The method includes administering a composition comprising an inhibitor of RANTES and/or an inhibitor of eotaxin to the subject in need thereof to treat the neurodegenerative disorder.

3 Claims, 17 Drawing Sheets

Specification includes a Sequence Listing.

(56) References Cited

OTHER PUBLICATIONS

Dasgupta, S. et al.; "Role of very-late antigen-4 (VLA-4) in myelin basic protein-primed T cell contact-induced expression of proinflammatory cytokines in microglial cells;" Journal of Biological Chemistry, vol. 278; Apr. 10, 2003; pp. 22424-22431.

Dasgupta, S. et al.; "Myelin basic protein-primed T cells of female but not male mice induce nitric-oxide synthase and proinflammatory cytokines in microglia: implications for gender bias in multiple sclerosis"; The Journal of Biological Chemistry, vol. 280; Sep. 23, 2005; pp. 32609-32617.

Dasgupta, S. et al.; "Gemfibrozil ameliorates relapsing-remitting experimental autoimmune encephalomyelitis independent of peroxisome proliferator-activated receptor-alpha"; Molecular Pharmacology, vol. 72; Jul. 11, 2007; pp. 934-946.

Dauer, W. et al.; "Parkinson's disease: mechanisms and models"; Neuron, vol. 39; Sep. 11, 2003; pp. 889-909.

Field, R. et al.; "Systemic challenge with the TLR3 agonist poly I:C induces amplified IFNalpha/beta and IL-1beta responses in the diseased brain and exacerbates chronic neurodegeneration"; Brain, Behavior, and Immunity, vol. 24; Aug. 1, 2010; pp. 996-1007.

Gendelman, H. E. et al.; "A Perspective on Roles Played by Innate and Adaptive Immunity in the Pathobiology of Neurodegenerative Disorders"; Journal of Neuroimmune Pharmacology, vol. 10; Dec. 2015; pp. 645-650.

Ghosh, A. et al.; "Selective inhibition of NF-kappaB activation prevents dopaminergic neuronal loss in a mouse model of Parkinson's disease"; Proceedings of the National Academy of Sciences of the United States of America, vol. 104; Nov. 20, 2007; pp. 18754-18759.

Ghosh, A. et al.; "Simvastatin inhibits the activation of p21ras and prevents the loss of dopaminergic neurons in a mouse model of Parkinson's disease"; The Journal of Neuroscience, vol. 29; Oct. 28, 2009; pp. 13543-13556.

Hu, S. et al.; "Inhibition of microglial cell RANTES production by IL-10 and TGF-beta"; Journal of Leukocyte Biology, vol. 65; Jun. 1999; pp. 815-821.

Jana, M. et al.; "Ligation of CD40 stimulates the induction of nitric-oxide synthase in microglial cells" Journal of Biological Chemistry, vol. 276; Sep. 2001; pp. 44527-44533.

Jana, M. et al.; "Regulation of tumor necrosis factor-alpha expression by CD40 ligation in BV-2 microglial cells"; Journal of Neurochemistry, vol. 80; Jan. 1, 2002; pp. 197-206.

Jana, M. et al.; "Involvement of phosphatidylinositol 3-kinase-mediated up-regulation of I kappa B alpha in anti-inflammatory effect of gemfibrozil in microglia"; The Journal of Immunology, vol. 179; Sep. 15, 2007; pp. 4142-4152.

Khasnavis, S. et al.; "Sodium Benzoate, a Metabolite of Cinnamon and a Food Additive, Upregulates Neuroprotective Parkinson Disease Protein DJ-1 in Astrocytes and Neurons"; Journal of Neuroimmune Pharmacology, vol. 7; Jun. 2012; 21 pages.

Khasnavis, S. et al.; "Protection of dopaminergic neurons in a mouse model of Parkinson's disease by a physically-modified saline containing charge-stabilized nanobubbles"; Journal of Neuroimmune Pharmacology, vol. 9; Mar. 1, 2014; pp. 218-232.

Khasnavis, S. et al.; "Cinnamon treatment upregulates neuroprotective proteins Parkin and DJ-1 and protects dopaminergic neurons in a mouse model of Parkinson's disease"; Journal of Neuroimmune Pharmacology, vol. 9; Sep. 2014; pp. 569-581.

Lee, J. K. et al.; "Regulator of G-protein signaling-10 negatively regulates NF-kappaB in microglia and neuroprotects dopaminergic neurons in hemiparkinsonian rats"; The Journal of Neuroscience, vol. 31; Aug. 17, 2011; pp. 11879-11888.

Martin, H. L. et al.; "Evidence for a role of adaptive immune response in the disease pathogenesis of the MPTP mouse model of Parkinson's disease"; Glia, vol. 64, No. 3; Mar. 2016; pp. 386-396.

Mondal, S. et al.; "Testing NF-kappaB-based therapy in hemiparkinsonian monkeys"; Journal of Neuroimmune Pharmacology, vol. 7; Sep. 2012; pp. 544-556.

Nitsch, R. et al.; "Direct impact of T cells on neurons revealed by two-photon microscopy in living brain tissue"; The Journal of Neuroscience, vol. 24; Mar. 10, 2004; pp. 2458-2464.

Olanow, C. W. et al.; "Etiology and pathogenesis of Parkinson's disease"; Annual Review of Neuroscience, vol. 22; Mar. 1999; pp. 123-144.

Pahan, P. et al.; "Can cinnamon bring aroma in Parkinson's disease treatment?"; Neural Regeneration Research, vol. 10; Jan. 2015; pp. 30-32.

Perry, V. H. et al.; "Systemic infections and inflammation affect chronic neurodegeneration"; Nature Reviews Immunology, vol. 7; Feb. 2007; pp. 161-167.

Reynolds, A. D. et al.; "Regulatory T cells attenuate Th17 cell-mediated nigrostriatal dopaminergic neurodegeneration in a model of Parkinson's disease"; Journal of Immunology, vol. 184; Jan. 27, 2010; pp. 2261-2271.

Roy, A. et al.; "Up-regulation of microglial CD11b expression by nitric oxide;" The Journal of Biological Chemistry, vol. 281; May 26, 2006; pp. 14971-14980.

Roy, A. et al.; "Reactive oxygen species up-regulate CD11b in microglia via nitric oxide: Implications for neurodegenerative diseases"; Free Radical Biology and Medicine, vol. 45; Sep. 2008; pp. 686-699.

Roy, A. et al.; "Prospects of statins in Parkinson disease"; Neuroscientist, vol. 17; Jun. 2011; pp. 244-255.

Roy, A. et al.; "Sodium phenylbutyrate controls neuroinflammatory and antioxidant activities and protects dopaminergic neurons in mouse models of Parkinson's disease"; PLoS One, vol. 7; Jun. 2012; e38113; 18 pages.

Roy, A. et al.; "Regulation of cyclic AMP response element binding and hippocampal plasticity-related genes by peroxisome proliferator-activated receptor alpha"; Cell Reports, vol. 4; Aug. 29, 2013; pp. 724-737.

Roy, A. et al.; "HMG-CoA Reductase Inhibitors Bind to PPARalpha to Upregulate Neurotrophin Expression in the Brain and Improve Memory in Mice"; Cell Metabolism, vol. 22; Aug. 4, 2015; pp. 253-265.

Roy, A. et al.; "Attenuation of microglial RANTES by NEMO-binding domain peptide inhibits the infiltration of CD8(+) T cells in the nigra of hemiparkinsonian monkey"; Neuroscience, vol. 302; Aug. 27, 2015; pp. 36-46.

Saha et al.; "Up-regulation of BDNF in astrocytes by TNF-alpha: a case for the neuroprotective role of cytokine"; Journal of Neuroimmune Pharmacology, vol. 1; Sep. 2006; pp. 212-222.

Vila, M. et al.; "Genetic clues to the pathogenesis of Parkinson's disease"; Nature Medicine, vol. 10 Supplement; Jul. 2004; pp. S58-S62.

Wada, T. et al.; "Eotaxin contributes to renal interstitial eosinophilia"; Nephrology, dialysis, transplantation: official publication of the European Dialysis and Transplant Association—European Renal Association, vol. 14; Jan. 1999; pp. 76-80.

Wei, J. et al.; "Differences in microglia activation between rats-derived cell and mice-derived cell after stimulating by soluble antigen of IV larva from Angiostrongylus cantonensis in vitro"; Parasitology Research, vol. 112; Jan. 1, 2013; pp. 207-214.

Wu, D. C. et al.; "Blockade of microglial activation is neuroprotective in the 1-methyl-4-phenyl-1,2,3,6-tetrahydropyridine mouse model of Parkinson disease"; The Journal of Neuroscience, vol. 22; Mar. 1, 2002; pp. 1763-1771.

International Search Report dated May 24, 2017 for International Application No. PCT/EP2017/021541.

Sugasawa et al. "Gastric Cancer Cells Exploit CD4+Cell-Derived CCL5 for their Growth and Prevention of CD8+Cell-Involved Tumor Climination," Int. J. Cancer, vol. 122, (2008), pp. 2535-2541.

Dent et al., "Contribution of Eotaxin-1 to Eosinophil Chemotactic Activity of Moderate and Severe Asthmatic Sputum," Am. J. Respir Crit Care Med., vol. 169, (2001), pp. 1110-1117.

Office Action, issued in JP Application No. 2018-548106, dated Mar. 2, 2021.

* cited by examiner

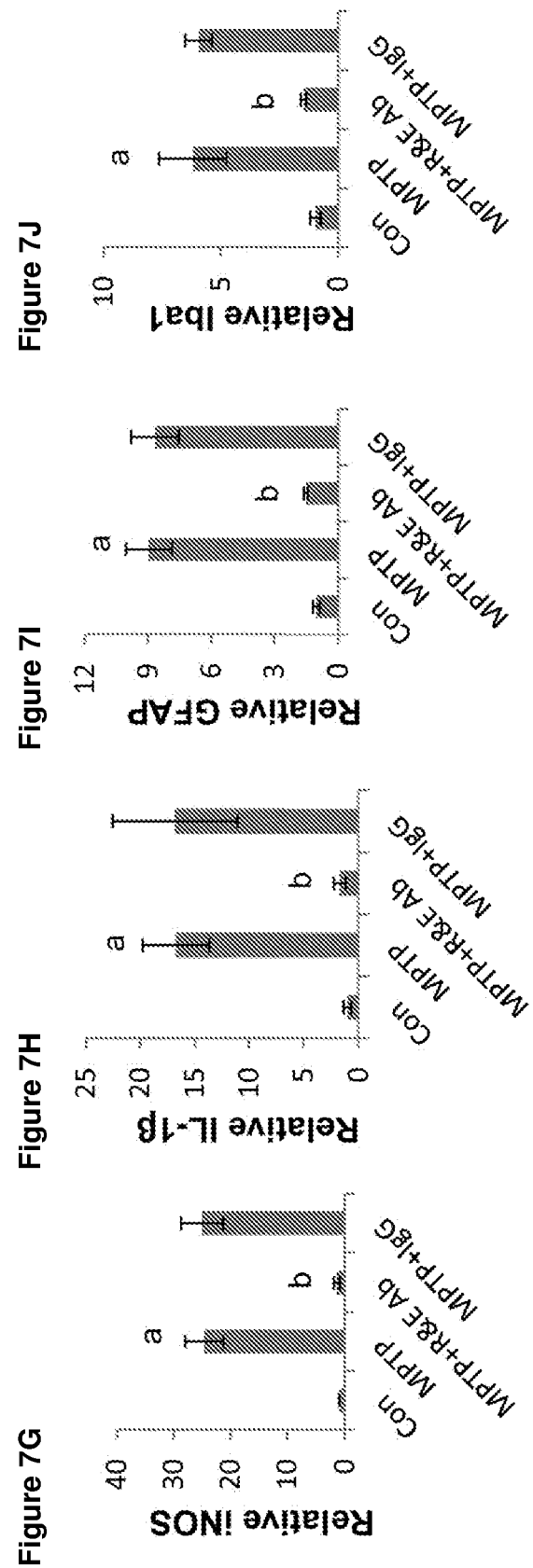

SEQUENCE LISTING

```
<160> NUMBER OF SEQ ID NOS: 18

<210> SEQ ID NO 1
<211> LENGTH: 25
<212> TYPE: DNA
<213> ORGANISM: Artificial Sequence
<220> FEATURE:
<223> OTHER INFORMATION: iNOS sense

<400> SEQUENCE: 1
cccttccgaa gtttctggca gcagc                                               25

<210> SEQ ID NO 2
<211> LENGTH: 25
<212> TYPE: DNA
<213> ORGANISM: Artificial Sequence
<220> FEATURE:
<223> OTHER INFORMATION: iNOS antisense

<400> SEQUENCE: 2
ggctgtcaga gcctcgtggc tttgg                                               25

<210> SEQ ID NO 3
<211> LENGTH: 21
<212> TYPE: DNA
<213> ORGANISM: Artificial Sequence
<220> FEATURE:
<223> OTHER INFORMATION: IL-1B sense

<400> SEQUENCE: 3
ctccatgagc tttgtacaag g                                                   21

<210> SEQ ID NO 4
<211> LENGTH: 20
<212> TYPE: DNA
<213> ORGANISM: Artificial Sequence
<220> FEATURE:
<223> OTHER INFORMATION: IL-1B antisense

<400> SEQUENCE: 4
tgctgatgta ccagttgggg                                                     20

<210> SEQ ID NO 5
<211> LENGTH: 19
<212> TYPE: DNA
<213> ORGANISM: Artificial Sequence
<220> FEATURE:
<223> OTHER INFORMATION: IL-6 sense

<400> SEQUENCE: 5
gacaactttg gcattgtgg                                                      19

<210> SEQ ID NO 6
<211> LENGTH: 19
<212> TYPE: DNA
<213> ORGANISM: Artificial Sequence
<220> FEATURE:
<223> OTHER INFORMATION: IL-6 antisense

<400> SEQUENCE: 6
```
atgcagggat gatgttctg                                                    19

<210> SEQ ID NO 7
<211> LENGTH: 32
<212> TYPE: DNA
<213> ORGANISM: Artificial Sequence
<220> FEATURE:
<223> OTHER INFORMATION: TNFa sense

<400> SEQUENCE: 7
ttctgtctac tgaacttcgg ggtgatcggt cc                                     32

<210> SEQ ID NO 8
<211> LENGTH: 32
<212> TYPE: DNA
<213> ORGANISM: Artificial Sequence
<220> FEATURE:
<223> OTHER INFORMATION: TNFa antisense

<400> SEQUENCE: 8
gtatgagata gcaaatcggc tgacggtgtg gg                                     32

<210> SEQ ID NO 9
<211> LENGTH: 20
<212> TYPE: DNA
<213> ORGANISM: Artificial Sequence
<220> FEATURE:
<223> OTHER INFORMATION: RANTES sense

<400> SEQUENCE: 9
atacgcttcc ctgtcatcgc                                                   20

<210> SEQ ID NO 10
<211> LENGTH: 20
<212> TYPE: DNA
<213> ORGANISM: Artificial Sequence
<220> FEATURE:
<223> OTHER INFORMATION: RANTES antisense

<400> SEQUENCE: 10
ttgggtttcg tggtcgagag                                                   20

<210> SEQ ID NO 11
<211> LENGTH: 20
<212> TYPE: DNA
<213> ORGANISM: Artificial Sequence
<220> FEATURE:
<223> OTHER INFORMATION: Eotaxin sense

<400> SEQUENCE: 11
agctagtcgg gagagcctac                                                   20

<210> SEQ ID NO 12
<211> LENGTH: 20
<212> TYPE: DNA
<213> ORGANISM: Artificial Sequence
<220> FEATURE:
<223> OTHER INFORMATION: Eotaxin antisense

<400> SEQUENCE: 12
aaggaagtga ccgtgagcag                                                   20

<210> SEQ ID NO 13
<211> LENGTH: 25
<212> TYPE: DNA
<213> ORGANISM: Artificial Sequence -continued

```
<220> FEATURE:
<223> OTHER INFORMATION: CD11b sense

<400> SEQUENCE: 13
gtgaggattc ctacgggacc caggt                                            25

<210> SEQ ID NO 14
<211> LENGTH: 25
<212> TYPE: DNA
<213> ORGANISM: Artificial Sequence
<220> FEATURE:
<223> OTHER INFORMATION: CD11b antisense

<400> SEQUENCE: 14
ggcgtacttc acaggcagct ccaac                                            25

<210> SEQ ID NO 15
<211> LENGTH: 20
<212> TYPE: DNA
<213> ORGANISM: Artificial Sequence
<220> FEATURE:
<223> OTHER INFORMATION: GFAP sense

<400> SEQUENCE: 15
ggcgctcaat gctggcttca                                                  20

<210> SEQ ID NO 16
<211> LENGTH: 20
<212> TYPE: DNA
<213> ORGANISM: Artificial Sequence
<220> FEATURE:
<223> OTHER INFORMATION: GFAP antisense

<400> SEQUENCE: 16
tctgcctcca gcctcaggtt                                                  20

<210> SEQ ID NO 17
<211> LENGTH: 20
<212> TYPE: DNA
<213> ORGANISM: Artificial Sequence
<220> FEATURE:
<223> OTHER INFORMATION: GADPH sense

<400> SEQUENCE: 17
ggtgaaggtc ggtgtgaacg                                                  20

<210> SEQ ID NO 18
<211> LENGTH: 20
<212> TYPE: DNA
<213> ORGANISM: Artificial Sequence
<220> FEATURE:
<223> OTHER INFORMATION: GADPH antisense

<400> SEQUENCE: 18
ttggctccac ccttcaagtg                                                  20
```

COMPOSITIONS AND METHODS FOR TREATING PARKINSON'S DISEASE

RELATED APPLICATIONS

This application claims the benefit under 35 U.S.C. § 371 of International Application No. PCT/US2017/021541, filed Mar. 9, 2017, which claims the benefit of U.S. Provisional Application No. 62/307,072, filed Mar. 11, 2016, which applications are incorporated by reference herein in their entirety.

SEQUENCE LISTING

The instant application contains a Sequence Listing which has been submitted electronically in ASCII format and is hereby incorporated by reference in its entirety. The ASCII copy, created on Mar. 2, 2017, is named 14904-202 sequence listing_ST25.txt and is approximately 4 KB in size.

BACKGROUND

1. Technical Field

The present invention is directed to compositions and methods for reducing RANTES (regulated on activation, normal T cell expressed and secreted) activation and/or eotaxin activation in a subject by administering a composition comprising an inhibitor of RANTES and/or an inhibitor of eotaxin to the subject in need thereof, and in particular, to subjects having Parkinson's disease.

2. Background Information

Parkinson's disease (PD) is the most common neurodegenerative movement disorder characterized by progressive loss of DA neurons in the ventral midbrain. Clinically, PD is characterized by tremor, bradykinesia, rigidity, and postural instability (1, 2). Pathologically, it is indicated by gliosis and progressive degeneration of the dopaminergic neurons associated with the presence of intracytoplasmic inclusions (Lewy bodies) in the substantia nigra pars compacta (SNpc) (3). Although the etiology is poorly understood, PD is regulated by the adaptive arm of the immune system and a number of recent studies have shown the involvement of inflammatory T cells in nigrostriatal degeneration (4-8). In a normal adult brain, the crosstalk between the peripheral immune system and the brain is transient, and there is no evidence that it leads to the brain inflammation. However in chronic neurodegeneration, when disease becomes more widespread involving distant regions of the brain and periphery, a growing body of evidence suggests that the brain-resident microglia are not only activated (9-11), but happen to be "primed" by the systemic inflammation, leading to the exaggerated synthesis of pro-inflammatory molecules (9, 12-15).

Earlier we have shown that microglial activation plays a critical role in the development of PD-related in mice and monkeys (10, 16-18). In numerous studies, we and others have shown that microglial cells can be activated by the chronic infiltration of peripheral inflammatory T cells (19-21). Accordingly, Brochard et al (5) have shown that both CD8+ and CD4+ T cells significantly invade the SNpc in postmortem specimens from patients with PD and in MPTP-intoxicated mice. They (5) have also demonstrated that removal of CD4+, but not of CD8+, T cells in mice greatly reduced MPTP-induced nigrostriatal dopamine cell death. According to Gendelman and colleagues (6), while Th17 cells exacerbate nigrostriatal dopaminergic neurodegeneration, regulatory T cells attenuate such neurodegeneration.

Although mechanisms leading to the infiltration of T cells into the CNS are poorly understood, recently we have seen marked upregulation of RANTES and eotaxin, chemokines that are involved in the infiltration of T cells and other immune cells, in vivo in the SNpc and the serum of MPTP-intoxicated monkey (7), suggesting that these chemokines may participate in nigrostriatal degeneration. Accordingly, here, we demonstrate rapid upregulation of RANTES and eotaxin in nigra and serum of MPTP-intoxicated mice. Furthermore, we also delineate that RANTES and eotaxin are upregulated in the SNpc of postmortem PD brains as compared to age-matched controls and that functional blocking antibodies against RANTES and/or eotaxin protects against nigrostriatal degeneration in MPTP-intoxicated mice. These results suggest that neutralization of RANTES and/or eotaxin may be beneficial for PD patients.

BRIEF SUMMARY

In some embodiments, a composition for the treatment of a neurodegenerative disorder is provided. The composition includes an inhibitor of RANTES and/or an inhibitor of eotaxin.

In some embodiments, a method of treating neurodegenerative disorders in a subject is provided. The method includes administering a composition comprising an inhibitor of RANTES and/or an inhibitor of eotaxin to the subject in need thereof to treat the neurodegenerative disorder.

BRIEF DESCRIPTION OF THE DRAWINGS

FIG. 1C, eotaxin). The protein expression of RANTES and eotaxin was monitored by Western blot (FIG. 1D). Actin was run as control. Bands were scanned and values (FIG. 1E, RANTES/Actin; FIG. 1F, Eotaxin/Actin) are presented as relative to control. Levels of RANTES and eotaxin were also measured in nigral homogenates by ELISA (FIG. 1G, RANTES; FIG. 1H, eotaxin). Levels of RANTES and eotaxin were also measured in serum by ELISA (FIG. 1I, RANTES; FIG. 1J, eotaxin). Results are mean+SEM of four mice (n=4) per group. $^a p<0.001$ vs control; $^b p<0.05$ vs control.

FIG. 2A) Male C57/BL6 mice (6-8 week old) were insulted with 20 mg/kg body wt MPTP (four injections at every 2 h interval). After 1 d, nigral sections were double-labeled (FIG. 2A, Iba-1 & RANTES; FIG. 2B, GFAP & RANTES). Cells positive for RANTES (FIG. 2C) were counted in two nigral sections (two images per slide) of each of five mice (n=5) per group in an Olympus IX81 fluorescence microscope using the MicroSuite imaging software. $^a p<0.001$ vs. control.

FIG. 3A) Male C57/BL6 mice (6-8 week old) were insulted with 20 mg/kg body wt MPTP (four injections at every 2 h interval). After 1 d, nigral sections were double-labeled (FIG. 3A, Iba-1 & eotaxin; FIG. 3B, GFAP & eotaxin). Cells positive for eotaxin (FIG. 3C) were counted in two nigral sections (two images per slide) of each of five mice (n=5) per group in an Olympus IX81 fluorescence microscope using the MicroSuite imaging software. $^a$p<0.001 vs. control.

FIG. 4B, Iba-1 & eotaxin). Cells positive for RANTES (FIG. 4C) and eotaxin (FIG. 4D) were counted in two nigral sections (two images per slide) of each of four brains (n=4) per group in an Olympus IX81 fluorescence microscope using the MicroSuite imaging software. $^a$p<0.001 vs. control.

FIG. 5A) Schematic presentation of treatment of MPTP-intoxicated mice with antibodies and related experiments. FIG. 5B) Male C57/BL6 mice (6-8 week old) were insulted with 20 mg/kg body wt MPTP (four injections at every 2 h interval). After 2 h of the last injection of MPTP, animals were treated with the combination of 20 μg/mouse anti-RANTES Ab and 20 μg/mouse anti-eotaxin Ab via i.p. injection. After 1 d of the last injection of MPTP, nigral sections were double-labeled for CD4 and TH. FIG. 5C) CD4-positive cells were counted in two ventral midbrain sections (Coordinates: Anteroposterior −4.04 mm from Bregma, dorsoventral 3.75 mm, mediolateral 1.25 mm) were double-labeled for CD4 and TH. FIG. 5C) CD4-positive cells were counted in two nigral sections (two images per slide) of each of five mice (n=5) per group in an Olympus IX81 fluorescence microscope using the MicroSuite imaging software. $^a$p<0.001 vs. control; $^b$p<0.001 vs. MPTP.

FIG. 6A) Male C57/BL6 mice (6-8 week old) were insulted with 20 mg/kg body wt MPTP (four injections at every 2 h interval). After 2 h of the last injection of MPTP, animals were treated with the combination of 20 μg/mouse anti-RANTES Ab and 20 μg/mouse anti-eotaxin Ab via i.p. injection. After 1 d of the last injection of MPTP, ventral midbrain sections (Coordinates: Anteroposterior −4.04 mm from Bregma, dorsoventral 3.75 mm, mediolateral 1.25 mm) were double-labeled for CD8 and TH. FIG. 6B) CD8-positive cells were counted in two nigral sections (two images per slide) of each of five mice (n=5) per group in an Olympus IX81 fluorescence microscope using the MicroSuite imaging software. $^a$p<0.001 vs. control; $^b$p<0.001 vs. MPTP.

FIG. 7A-7J. Neutralization of RANTES and eotaxin reduces the expression of proinflammatory molecules in the nigra of MPTP-intoxicated mice. Male C57/BL6 mice (6-8 week old) were insulted with 20 mg/kg body wt MPTP (four injections at every 2 h interval). After 2 h of the last injection of MPTP, animals were treated with the combination of 20 μg/mouse anti-RANTES Ab and 20 μg/mouse anti-eotaxin Ab via i.p. injection. After 1 d of the last injection of MPTP, the mRNA expression of iNOS, IL-1β, GFAP, and CD11b was monitored in the nigra by RT-PCR (FIG. 7AA) and real-time PCR (FIG. 7B, iNOS; FIG. 7C, IL-1β; FIG. 7D, GFAP; FIG. 7E, CD11b). Results are mean+SEM of four mice (n=4) per group. $^a$p<0.001 vs control; $^b$p<0.001 vs MPTP. After 1 d of the last injection of MPTP, the protein expression of iNOS, IL-1β, GFAP, and Iba1 was monitored in the nigra by Western blot (FIG. 7F). Actin was run as control. Bands were scanned and values (FIG. 7G, iNOS/Actin; FIG. 7H, IL-1β/Actin; FIG. 7I, GFAP/Actin; FIG. 7J, Iba1/Actin) are presented as relative to control. Results are mean+SEM of four mice (n=4) per group. $^a$p<0.001 vs control; $^b$p<0.001 vs MPTP.

FIG. 8B, GFAP & iNOS). Cells positive for iNOS (C), Iba-1 (FIG. 8D) and GFAP (FIG. 8E) were counted in two nigral sections (two images per slide) of each of five mice (n=5) per group in an Olympus IX81 fluorescence microscope using the MicroSuite imaging software. $^a$p<0.001 vs. control; $^b$p<0.001 vs. control.

FIG. 11B, pole test; FIG. 11C, number of movements; FIG. 11D, movement time; FIG. 11E, rest time; FIG. 11F, horizontal activity; FIG. 11G, total distance; FIG. 11H, stereotypy). Data are means±SEM of nine mice per group. $^a$p<0.001 vs control; $^c$p<0.05 vs control; $^b$p<0.001 vs MPTP; $^d$p<0.05 vs MPTP.

DETAILED DESCRIPTION

Definitions

Figure 1A:
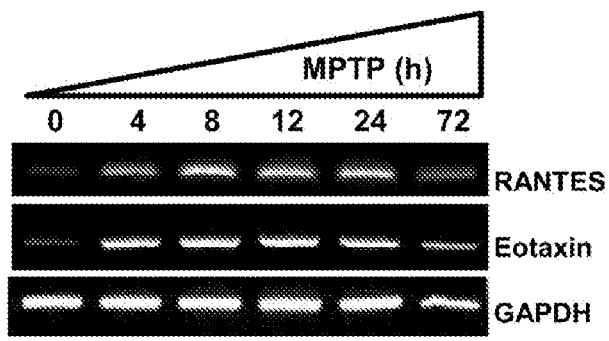
FIG. 1A-1J. Rapid upregulation of RANTES and eotaxin in nigra and serum of MPTP-intoxicated mice. Male C57/BL6 mice (6-8 week old) were insulted with 20 mg/kg body wt MPTP (four injections at every 2 h interval). After 4, 8, 12, 24, and 72 h of MPTP intoxication, the mRNA expression of RANTES and eotaxin in nigra was monitored by semi-quantitative RT-PCR (FIG. 1A) and real-time PCR (FIG. 1B, RANTES.

RANTES (regulated upon activation, normal T-cell expressed and secreted), a member of the C—C chemokine subfamily, is a ligand for a number of chemokine receptors including CCR1, CCR3, CCR5, CCR9 and DARC (Duffy Antigen Receptor for Chemokines) in humans. RANTES is a potent chemoattractant for T cells, monocytes, natural killer cells, basophils and eosinophils.

Eotaxin refers to a CC chemokine subfamily of eosinophil chemotactic proteins.

The term "inhibitor" refers to an agent that reduces expression of a polypeptide or polynucleotide target or binds to, partially or totally blocks stimulation, decreases, prevents, delays activation, inactivates, desensitizes, or down regulates the activity of a polypeptide or polynucleotide target. An inhibitor can neutralize activity (e.g., prevent binding and activation by a natural ligand) or actively reduce activity. Targets as used herein may include RANTES and/or eotaxin.

The term "antibody" refers to a polypeptide comprising a framework region from an immunoglobulin gene or fragments thereof that specifically binds and recognizes an antigen. Typically, the antigen-binding region of an antibody will be most critical in specificity and affinity of binding. The term "antibody" includes for example, monoclonal antibodies, human antibodies, humanized antibodies, camelised antibodies, chimeric antibodies, single-chain Fvs (scFv), disulfide-linked Fvs (sdFv), Fab fragments, F (ab') fragments, and anti-idiotypic (anti-Id) antibodies (including, e.g., anti-Id antibodies to antibodies of the invention), and epitope-binding fragments of any of the above. The antibodies can be of any isotype (e.g., IgG, IgE, IgM, IgD, IgA and IgY), class (e.g., IgGl, IgG2, IgG3, IgG4, IgAl and IgA2) or subclass. Both the light and heavy chains are divided into regions of structural and functional homology.

The phrase "neutralizing antibody" as used herein refers to an antibody that binds with a target polypeptide and neutralizes the biological activity of target polypeptide. Accordingly, an antibody that "inhibits" one or more of these target polypeptide functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (e.g., or when a control antibody of irrelevant specificity is present). An antibody that inhibits target polypeptide activity effects such a statistically significant decrease by at least 10% of the measured parameter, by at least 50%>, 80%> or 90%>, and in certain embodiments an antibody of the invention may inhibit greater than 95%, 98% or 99% of target polypeptide functional activity. Target polypeptides as used herein include RANTES and exotaxin.

"Treating", "treat", or "treatment" within the context of the instant invention, means an alleviation of symptoms associated with a disorder or disease, or halt of further progression or worsening of those symptoms, or prevention or prophylaxis of the disease or disorder. For example, within the context of this invention, successful treatment may include an alleviation of symptoms related to a neurological disorder such as Parkinson's disease or a halting in the progression of a neurological disease such as Parkinson's.

Prophylactic and Therapeutic Uses

Methods of treating a disease or disorder by administering a therapeutically effective amount of an inhibitor (e.g., a dose of an antibody which inhibits RANTES and/or eotaxin). In some embodiments, a therapeutically effective amount of an antibody or fragment thereof that specifically binds to RANTES and/or eotaxin may be administered. In some embodiments, a therapeutically effective amount of an inhibitor of RANTES may be administered. In some embodiments, a therapeutically effective amount of an inhibitor of eotaxin may be administered. In some embodiments, a therapeutically effective amount of an inhibitor of RANTES and an inhibitor of eotaxin may be administered simultaneously or sequentially. In some embodiments, one or more of the inhibitors may be an antibody or fragment thereof. In some embodiments, multiple administrations of one or more of the inhibitors may be administered.

An effective amount for a particular subject may vary depending on factors such as the condition being treated, the overall health of the subject, the method route and dose of administration and the severity of side effects (see, e.g., Maynard et al., (1996) A Handbook of SOPs for Good Clinical Practice, Interpharm Press, Boca Raton, Fla.; Dent (2001) Good Laboratory and Good Clinical Practice, Urch PubL, London, UK).

Rapid induction of RANTES and eotaxin in nigra and serum of MPTP-intoxicated mice:

To investigate the role of RANTES and eotaxin in the loss of invaluable dopaminergic neurons in MPTP-intoxicated mice, first, we examined whether the expression of these chemokines was induced in midbrains of affected mice. It is evident from FIG. 1A that MPTP intoxication led to time-dependent induction of RANTES and eotaxin mRNA expression in the SNpc. This induction was evident as early as 4 h of MPTP insult (FIG. 1A). However, the expression of RANTES and eotaxin decreased at 72 h of MPTP intoxication (FIG. 1A). These results were confirmed by real-time PCR (FIG. 1B-C).

Figure 1D:
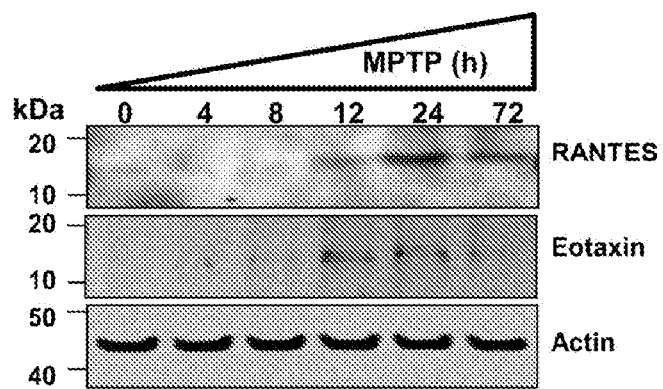
Figure 1B:
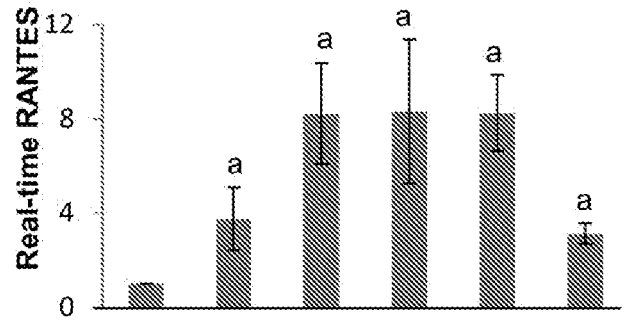
Figure 1C:
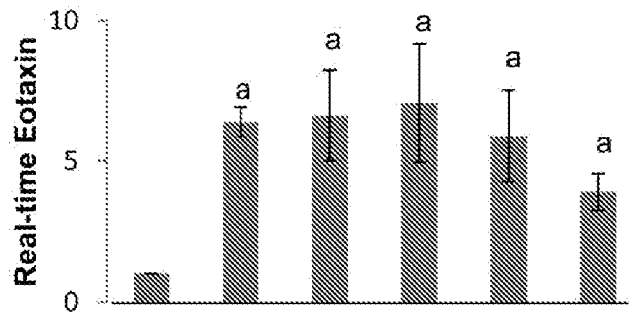
Figure 1G:
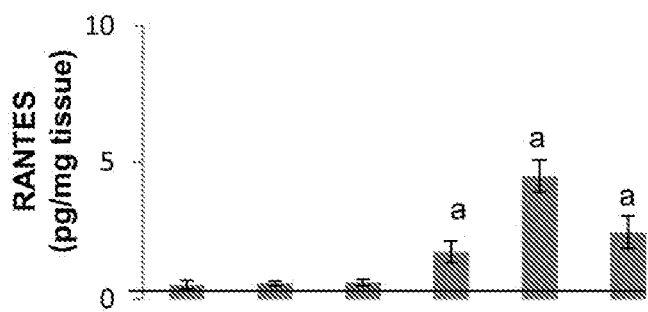
Figure 1H:
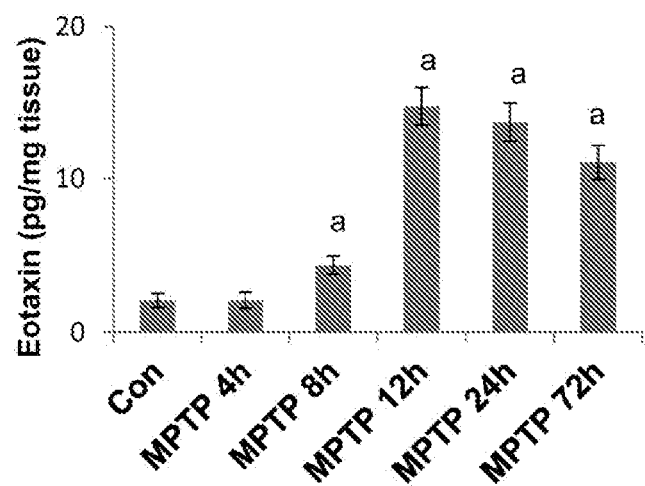
Figure 1E:
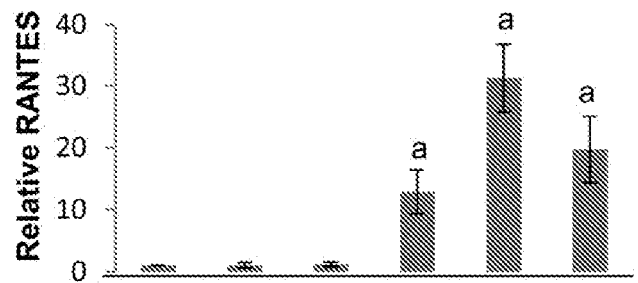
Figure 1F:
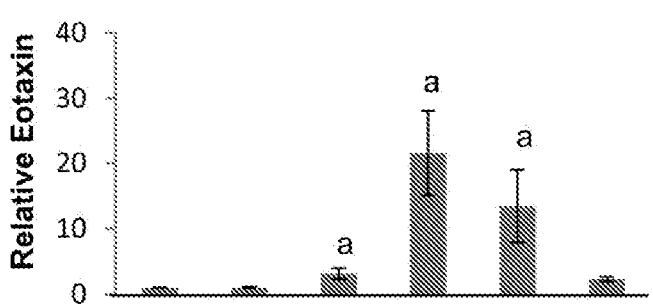
Figure 1I:
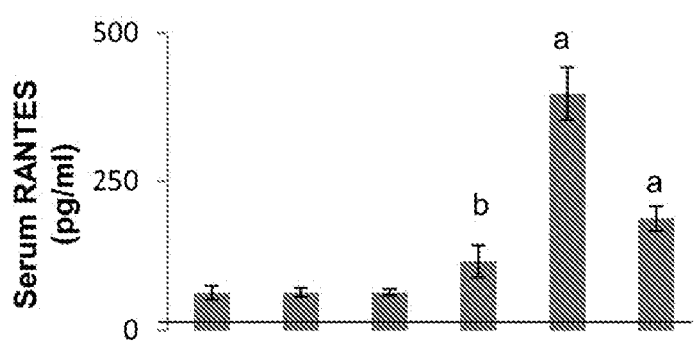
Figure 1J:
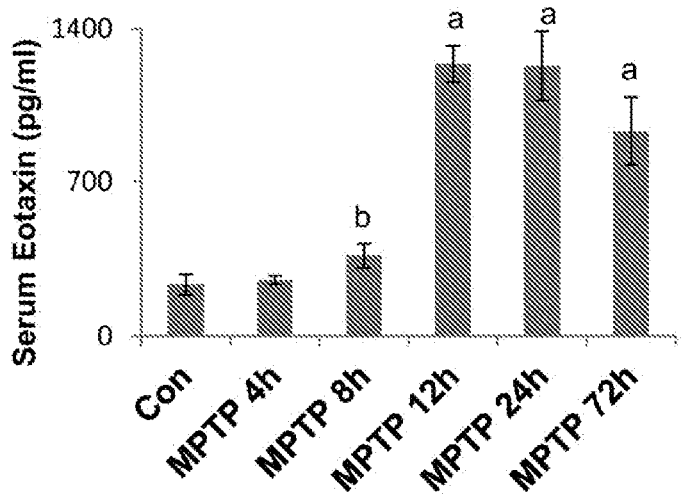

Similarly, Western blot results showed the induction of RANTES and eotaxin proteins in the nigra (FIG. 1D-F). Although RANTES was visible from 12 h of MPTP insult, significant increase in eotaxin was observed at 8 h (FIG. 1E-F). These results were also corroborated by ELISA of RANTES and eotaxin in nigral homogenates (FIG. 1G-H). Next, we monitored the levels of these chemokines in serum. While increase in RANTES was visible in serum from 12 h of MPTP intoxication and maximum at 24 h, eotaxin increase was prominent from 8 h and maximum at 12 h (FIG. 1I-J).

The role of RANTES and eotaxin in the progression of nigrostrial pathologies was also investigated. While MPTP intoxication markedly induced RANTES and eotaxin in serum and spleens of mice, levels of these chemokines started falling rapidly after 1 d of MPTP insult. Supplementation of recombinant RANTES and eotaxin induced never-ending T cell infiltration to the niagra, persistent glial activation, chronic nigral inflammation, uninterrupted loss of dopaminergic neurons and striatal fibers, nonstop striatal neurotransmitter loss, and impairment in locomotor activities, indicating the importance of the adaptive immune response in the progression of nigrostriatal pathologies in the MPTP mouse model.

Figure 2:
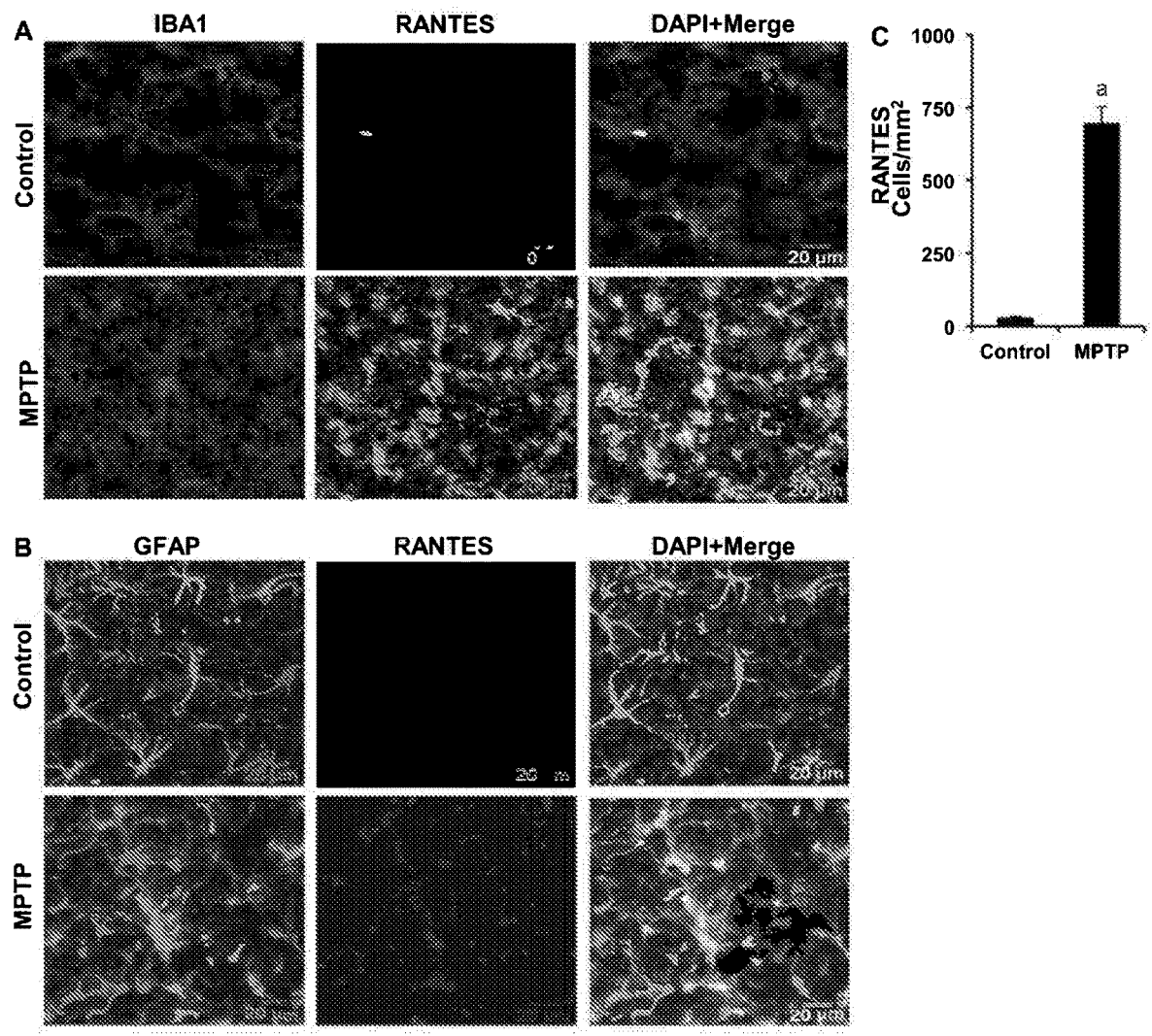
FIG. 2A-2C. Glial expression of RANTES in the SNpc of MPTP-intoxicated mice.
Figure 3:
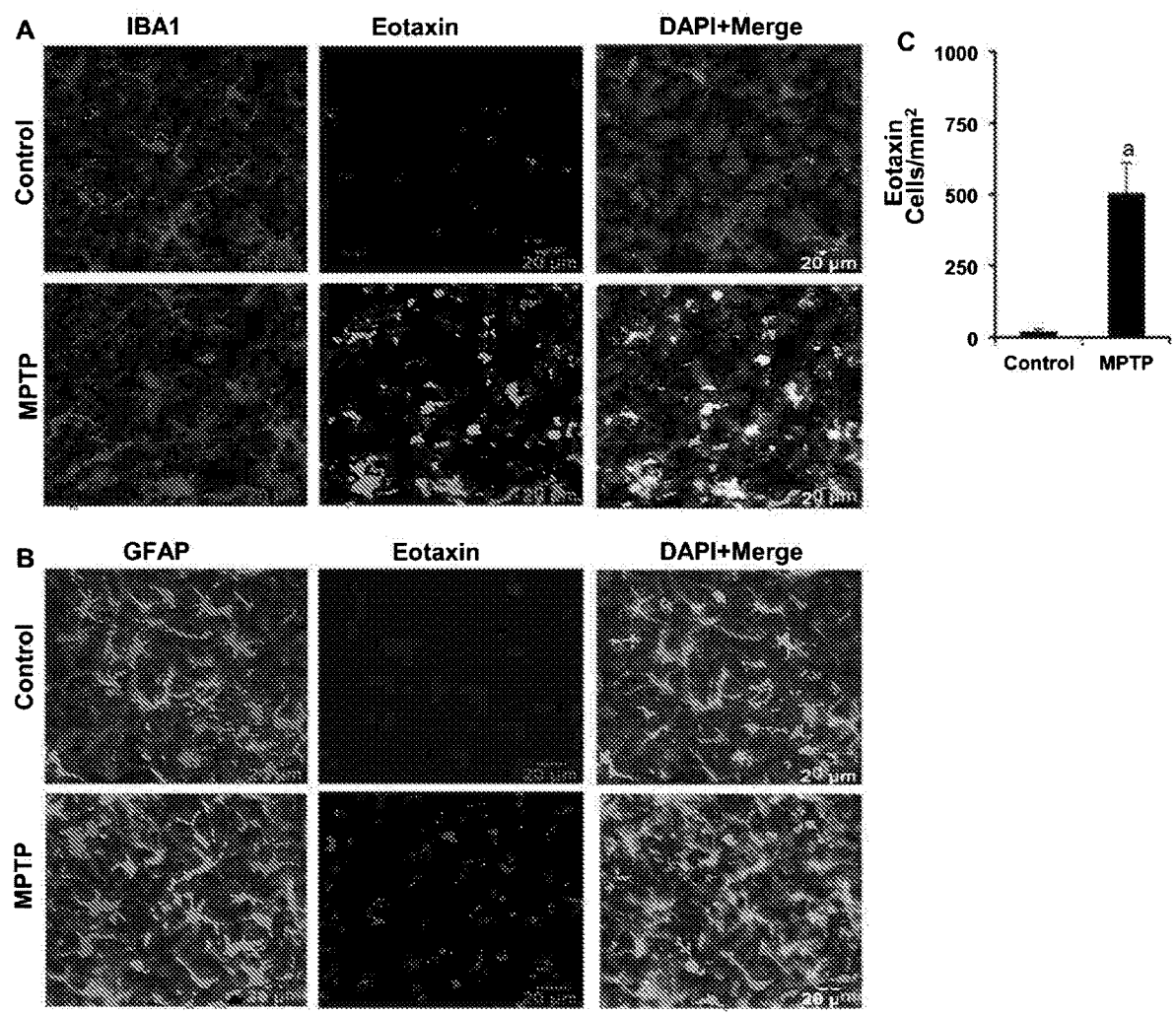
FIG. 3A-3C. Induction of eotaxin in the SNpc of MPTP-intoxicated mice.

Microglia in the nigra of MPTP-intoxicated mice and postmortem PD brains express RANTES and eotaxin: Since MPTP intoxication induced the level of RANTES and eotaxin in the nigra, next, we were interested to identify the cell type that produced these chemokines in the nigra. Recently chronic microglial activation is becoming a hallmark of different neurodegenerative disorders including PD (17, 18, 30, 32, 33). Therefore, we examined if microglia were capable of producing these chemokines in the nigra of MPTP-intoxicated mice. After 24 h of the last injection of MPTP, nigral sections were double-labeled for Iba-1 and RANTES. As evident from FIG. 2A-C, MPTP intoxication led to marked induction of RANTES in the nigra and most of these RANTES signals colocalized with Iba-1 (FIG. 2A). In addition, some RANTES signals also colocalized with GFAP-positive astroglia (FIG. 2B). Similarly, immunofluorescence analysis also reveals marked increase in eotaxin in the nigra of MPTP-intoxicated mice (FIG. 3A-C). Similar to RANTES, eotaxin also mostly colocalized with Iba-1-positive microglia (FIG. 3A) and partly with GFAP-positive astroglia (FIG. 3B).

Figure 4:
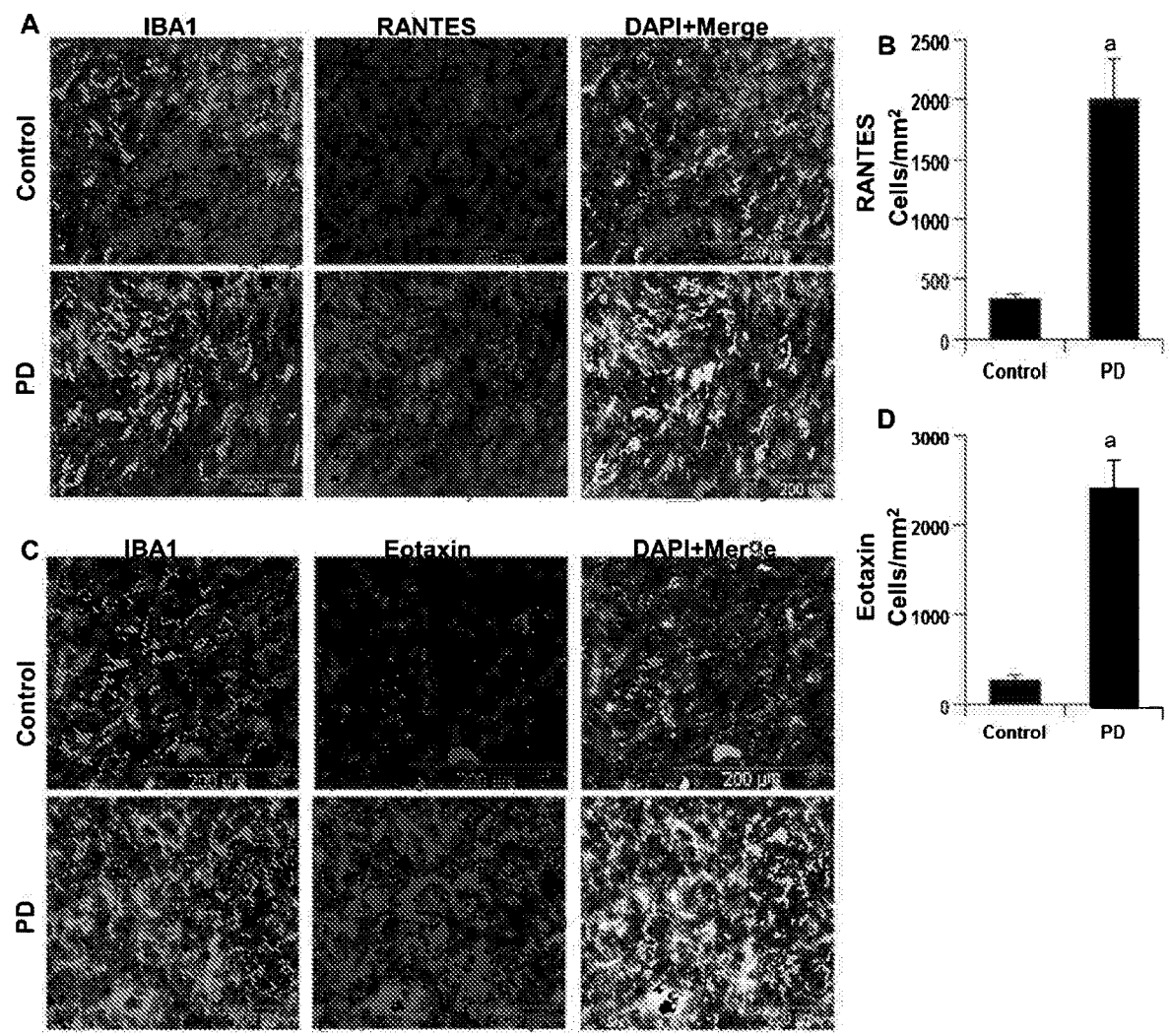
FIG. 4A-4D. Presence of RANTES and eotaxin in the SNpc of postmortem PD brains. Midbrain sections of postmortem PD brains and age-matched controls were double-labeled (FIG. 4A, Iba-1 & RANTES.
Figure 5:
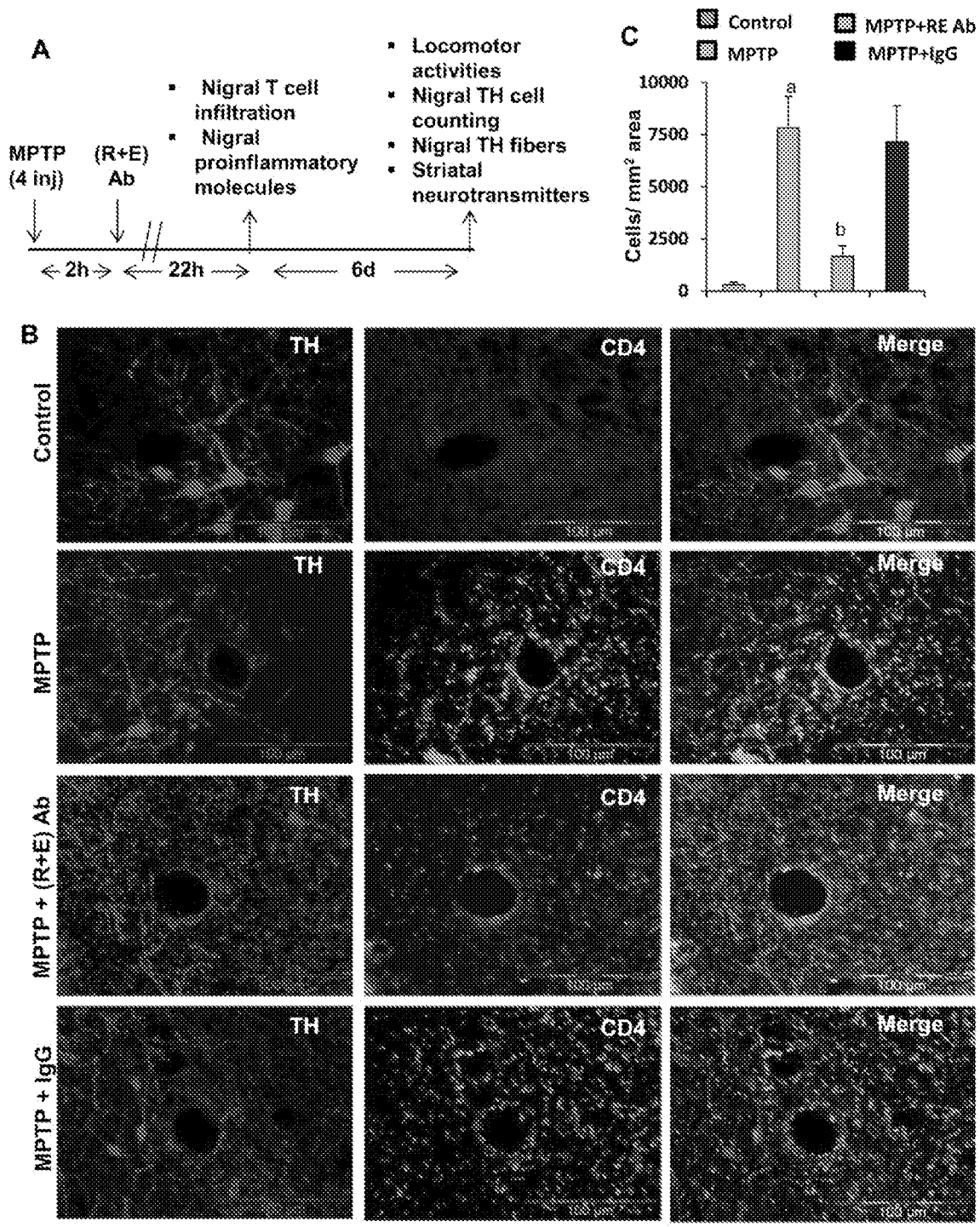
FIG. 5A-5C. Functional blocking antibodies against RANTES and eotaxin inhibit the infiltration CD4+ T cells into the nigra of MPTP-intoxicated mice.
Figure 6:
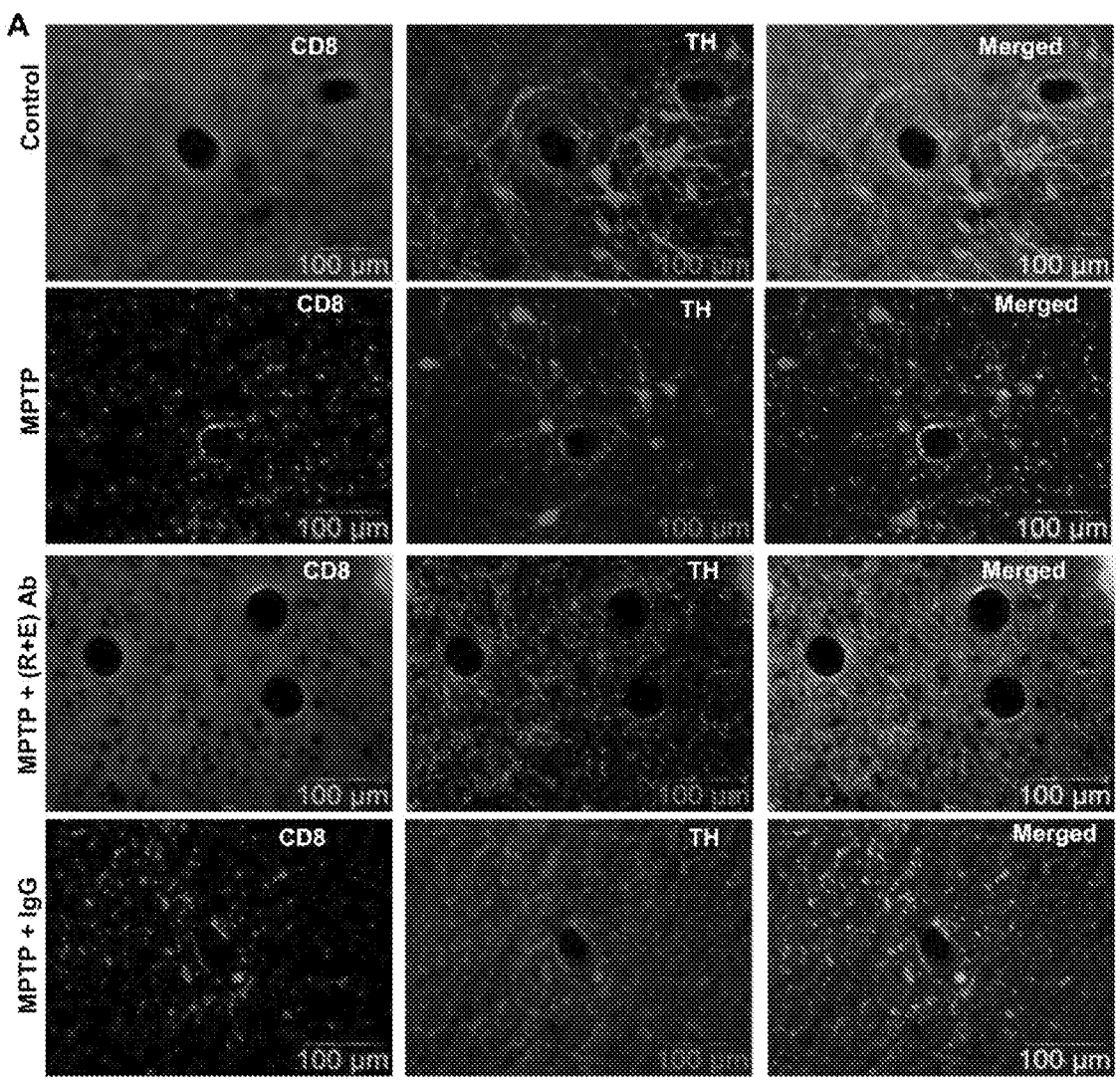
FIG. 6A-6B. Functional blocking antibodies against RANTES and eotaxin inhibit the infiltration of CD8$^+$ T cells into the nigra of MPTP-intoxicated mice.
Figure 6:
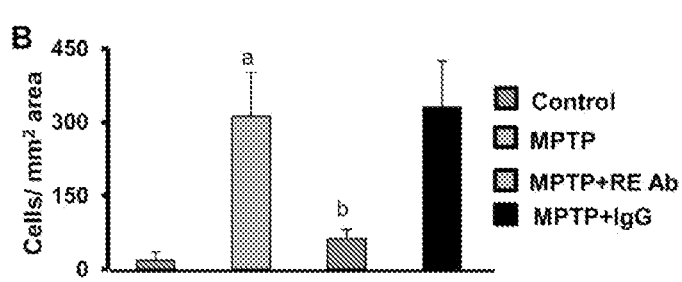

Next, to understand the role of RANTES and eotaxin in nigrostriatal degeneration in PD, nigral sections from postmortem PD brains and age-matched individuals were immunolabeled for RANTES and eotaxin. Since microglia is the major cell type in the nigra of MPTP-intoxicated mice that express these chemokines, sections were double-labeled for RANTES/eotaxin and Iba-1. Levels of both RANTES and eotaxin were markedly higher in the nigra of PD brain compared to age-matched controls (FIG. 4A-D). We also noticed greater Iba-1 expression (microglial activation) in the nigra of PD compared to age matched controls (FIGS. 4A & 4C). Iba-1—positive cells were also positive for both RANTES (FIG. 4A) and eotaxin (FIG. 4C) in the nigra of PD subjects. Functional blocking antibodies against RANTES and eotaxin suppresses the infiltration of T cells into the nigra and attenuates the expression of proinflammatory molecules in the nigra of MPTP-intoxicated mice: Since we observed rapid increase in RANTES and eotaxin in the serum of MPTP-intoxicated mice, to understand the role of these chemokines in nigrostriatal degeneration, mice were treated once with the combination of functional blocking antibodies against both RANTES and eotaxin via i.p. injection (FIG. 5A). Chemokines like RANTES and eotaxin are known to induce the migration and homing of inflammatory lymphoid cells such as T cells and monocytes in the site of inflammation. Because substantia nigra is a primary target of neurodegeneration in PD, we determined whether MPTP intoxication induced the infiltration of inflammatory T cells in the nigra. Our dual immunofluorescence analyses of CD4 (green) and tyrosine hydroxylase (TH) (red) clearly displayed a typical CD4-immunoreactive inflammatory cuffing in the nigra of MPTP-intoxicated, but not control, mice (FIG. 5B-C). This is in consistent to that observed in the nigra of PD patients (5). Recently we have demonstrated infiltration of CD8+ T cells into the nigra of hemiparkinsonian monkeys (7). Therefore, we also analyzed infiltration of CD8+ T cells and found CD8+ inflammatory cuffing in the nigra of MPTP-insulted mice (FIG. 6A-B). However, as compared to CD4+ T cells, nigral infiltration of CD8+ cells was much less in MPTP-intoxicated mice (FIG. 5B-C & FIG. 6A-B). Nevertheless, treatment with neutralizing antibodies against RANTES and eotaxin strongly suppressed the infiltration of both CD4+(FIG. 5B-C) and CD8+(FIG. 6A-B) T cells in the nigra of MPTP-intoxicated mice. These results were specific as normal IgG had no such inhibitory effect (FIGS. 5-6). These results suggest that the infiltration of peripheral lymphocytes into the nigra of MPTP-insulted mice depends on RANTES and eotaxin.

Figure 7A:
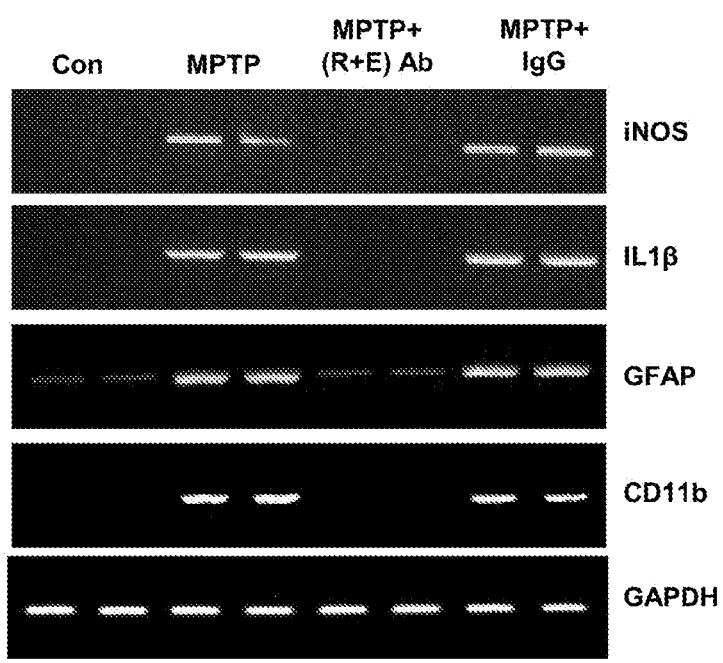
Figure 7F:
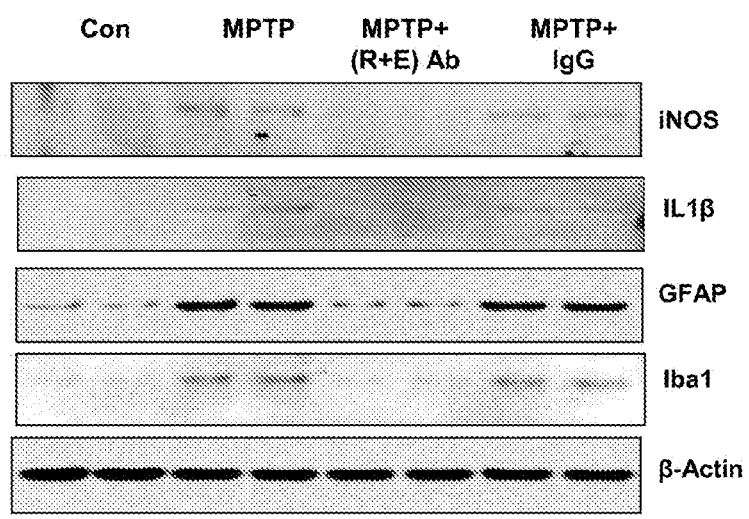
Figure 7B:
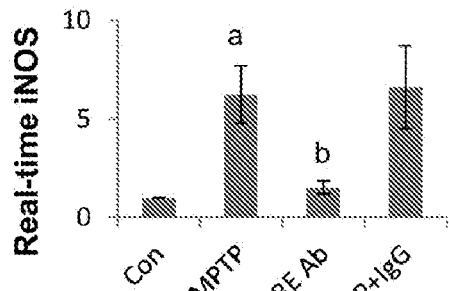
Figure 7C:
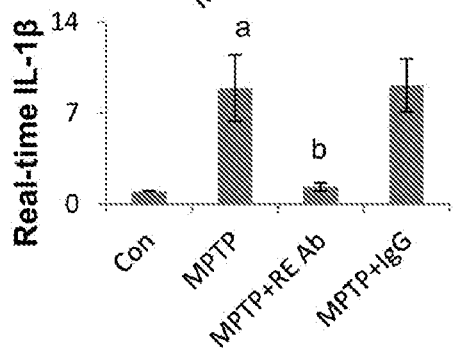
Figure 7D:
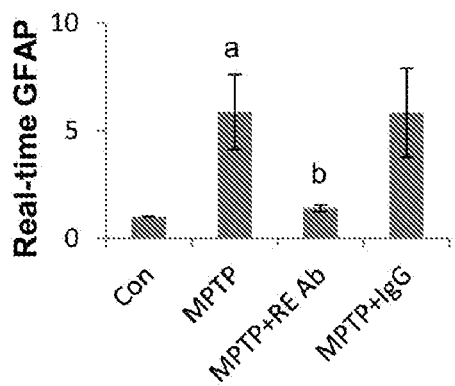
Figure 7E:
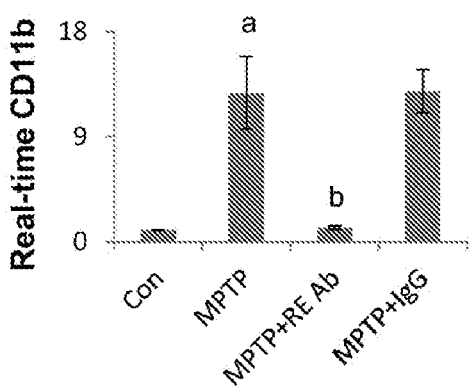
Figure 8:
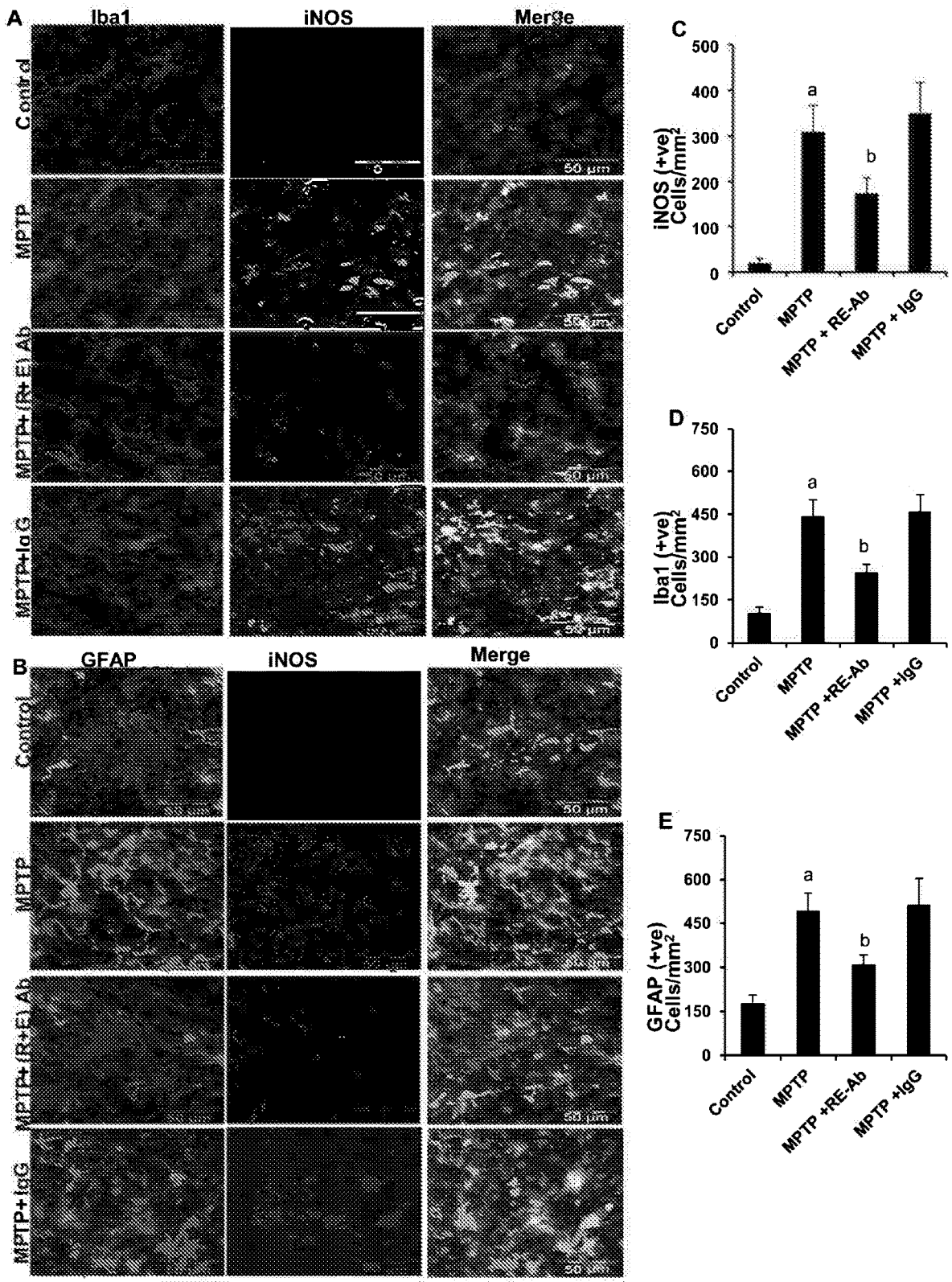
FIG. 8A-8E. Neutralization of RANTES and eotaxin decreases glial activation in the nigra of MPTP-intoxicated mice. Male C57/BL6 mice (6-8 week old) were insulted with 20 mg/kg body wt MPTP (four injections at every 2 h interval). After 2 h of the last injection of MPTP, animals were treated with the combination of 20 μg/mouse anti-RANTES Ab and 20 μg/mouse antieotaxin Ab via i.p. injection. After 1 d of the last injection of MPTP, nigral sections were double-labeled (FIG. 8A, Iba-1 & iNOS.

Infiltration of inflammatory T cells into the site of injury eventually triggers the production of a wide range of proinflammatory molecules (5, 8, 19, 30). Because neutralizing antibodies against RANTES and eotaxin inhibited the infiltration of T cells in vivo in the nigra of MPTP-intoxicated mice, we examined whether these antibodies were able to suppress the expression of various proinflammatory molecules in the nigra. As shown by semi-quantitative RT-PCR (FIG. 6A) and quantitative real-time PCR (FIG. 7B-E) experiments, MPTP intoxication led to marked increase in mRNA expression of iNOS, IL-1β, GFAP (astroglial marker), and CD11b (microglial marker) in the midbrain. However, neutralizing antibodies against RANTES and eotaxin, but not control IgG, strongly inhibited MPTP-induced expression of iNOS (FIG. 6A&B), IL-1β (FIG. 7A&C), GFAP (FIG. 7A&D), and CD11b (FIG. 7A&E) mRNAs in vivo in the nigra. Similarly, Western blot results also show increase in iNOS, IL-16, GFAP, and Iba1 in the nigra by MPTP insult and attenuation of these proinflammatory markers (FIG. 7F-J) by treatment with neutralizing antibodies against RANTES and eotaxin. Double-label immunofluorescence analysis also shows that MPTP intoxication led to marked increase in nigral iNOS protein expression and that this iNOS colocalized strongly with Iba1-positive microglia (FIG. 8A) and partly with GFAP-positive astroglia (FIG. 8B). Similar to mRNA and Western blot results, treatment of MPTP-intoxicated mice with neutralizing antibodies against RANTES and eotaxin, but not control IgG, led to the suppression of iNOS protein (FIG. 8A-C). Recently glial activation is being considered as a pathological hallmark in PD and other neurodegenerative disorders (17, 18, 30, 32). As evident from immunofluorescence analysis of Iba1 and GFAP in nigral sections, MPTP intoxication led to increase in nigral Iba1 and GFAP protein expression and neutralizing antibodies against RANTES and eotaxin suppressed MPTP-induced expression of Iba1 (FIG. 8A&D) and GFAP (FIG. 8A&E). These results suggest that neutralization of RANTES and eotaxin suppresses the expression of proinflammatory molecules and reduces glial activation in the nigra of MPTP-intoxicated mice.

Figure 9A:
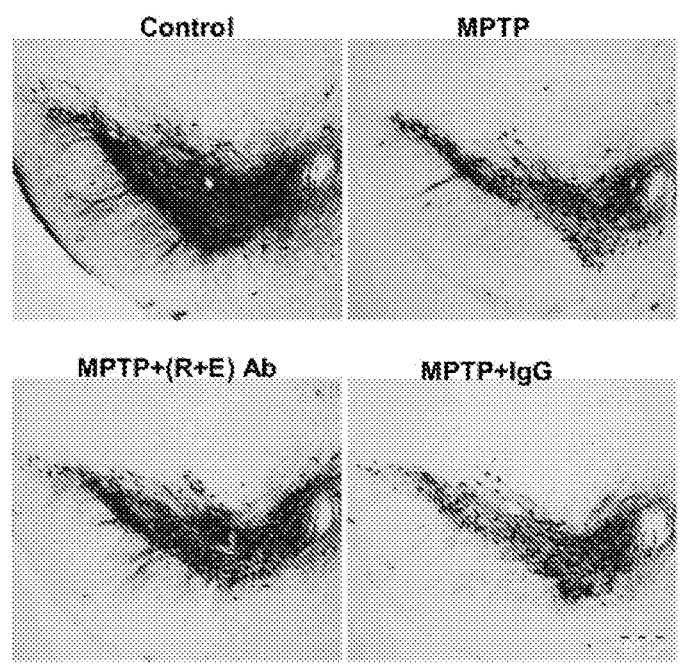
FIG. 9A-9E. Neutralization of RANTES and eotaxin protects dopaminergic neurons in the nigra of MPTP-intoxicated mice. Male C57/BL6 mice (6-8 week old) were insulted with 20 mg/kg body wt MPTP (four injections at every 2 h interval). After 2 h of the last injection of MPTP, animals were treated with the combination of 20 μg/mouse anti-RANTES Ab and 20 μg/mouse anti-eotaxin Ab via i.p. injection. After 7 d of the last injection of MPTP, nigral sections were stained for TH (FIG. 9A). Magnified image TH-stained SNpc (FIG. 9B). TH neurons were counted by stereology using the STEREO INVESTIGATOR software (FIG. 9C). Results are mean+SEM of five mice (n=5) per group. $^a$p<0.001 vs control; $^b$p<0.001 vs MPTP. Nigral homogenates were immunoblotted for TH (FIG. 9D). Actin was run as control. Bands were scanned and values (TH/Actin) are presented as relative to control (FIG. 9E). Results are mean+SEM of four mice (n=4) per group. $^a$p<0.001 vs control; $^b$p<0.001 vs MPTP.
Figure 9B:
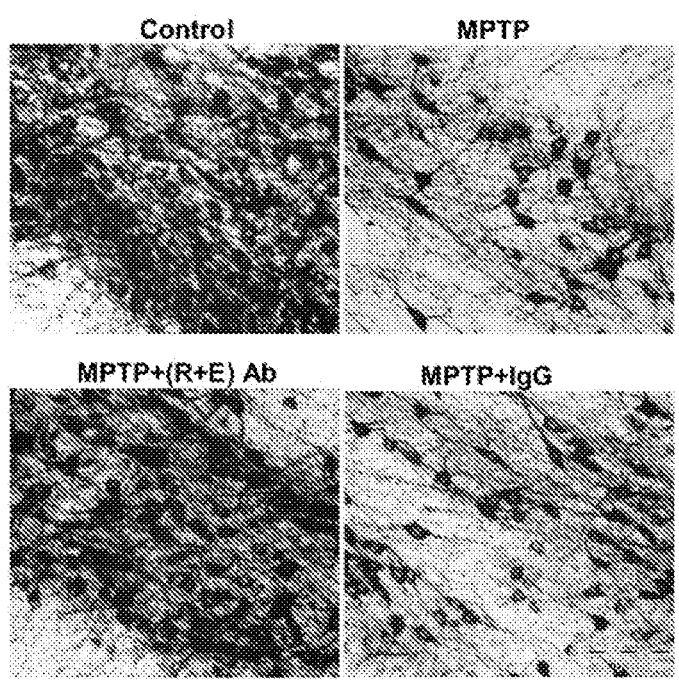
Figure 9D:
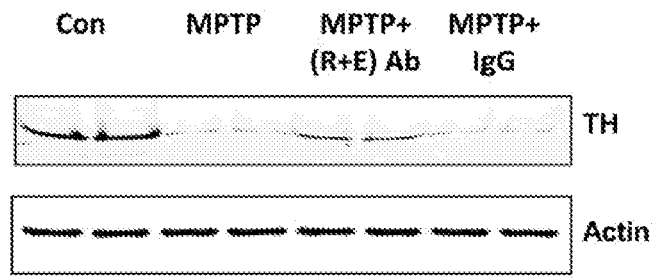
Figure 9C:
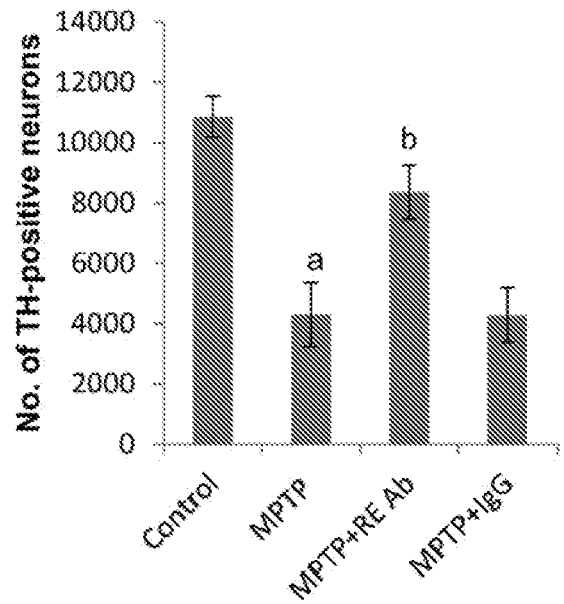
Figure 9E:
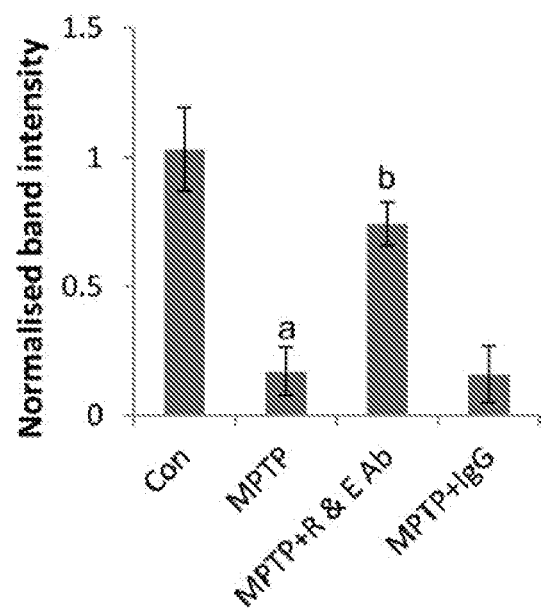
Figure 10A:
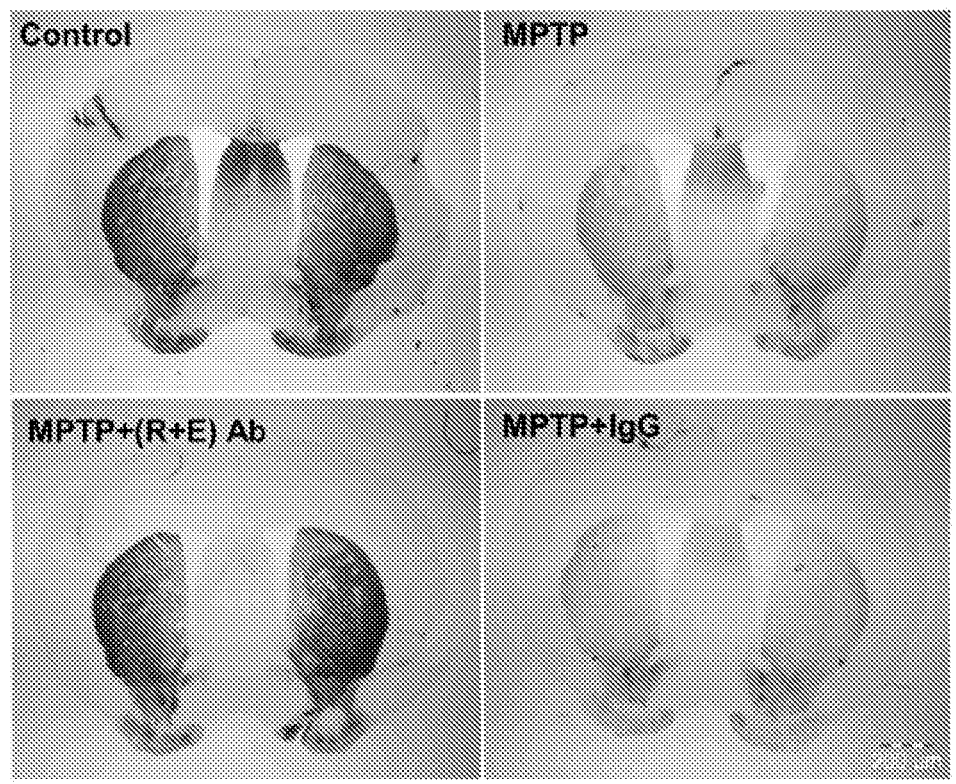
FIG. 10A-10E. Neutralization of RANTES and eotaxin protects TH fibers and restores neurotransmitters in the striatum of MPTP-intoxicated mice. Male C57/BL6 mice (6-8 week old) were insulted with 20 mg/kg body wt MPTP (four injections at every 2 h interval). After 2 h of the last injection of MPTP, animals were treated with the combination of 20 μg/mouse anti-RANTES Ab and 20 μg/mouse anti-eotaxin Ab via i.p. injection. After 7 d of the last injection of MPTP, striatal sections were stained for TH (FIG. 10A) followed by quantification of TH-positive fibers (FIG. 10B). Concentrations of dopamine (FIG. 10C), DOPAC (FIG. 10D) and HVA (FIG. 10E) were measured in the striatum by HPLC. Results are mean+SEM of five mice (n=5) per group. $^a$p<0.001 vs control; $^b$p<0.001 vs MPTP.
Figure 10B:
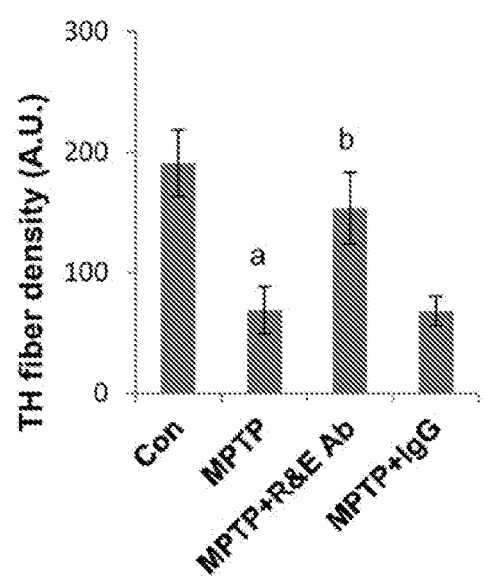
Figure 10C:
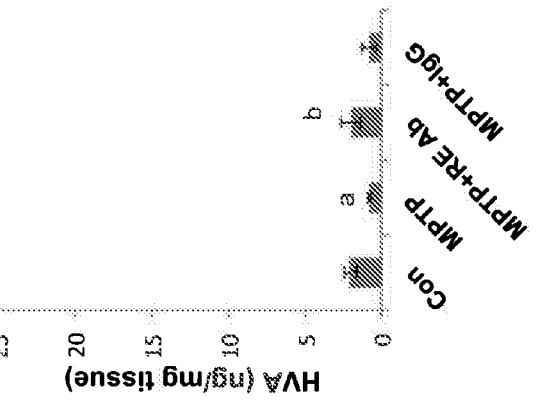
Figure 10D:
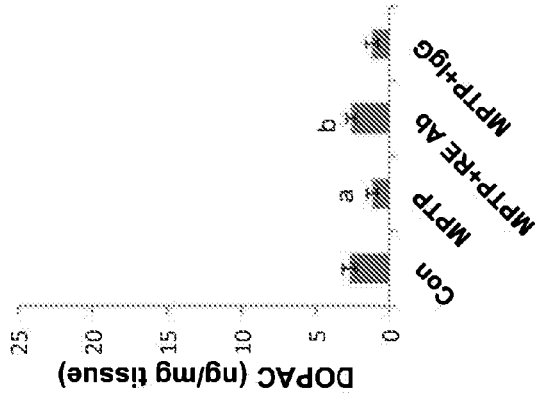
Figure 10E:
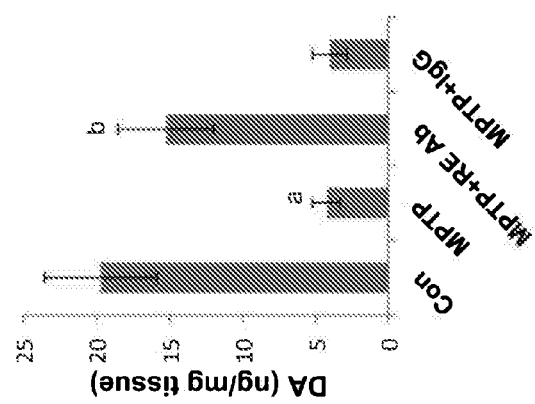

Functional blocking antibodies against RANTES and eotaxin protect against MPTP-induced neurodegeneration: Since neutralization of RANTES and eotaxin inhibited glial activation and associated neuroinflammation in the nigra of MPTP-intoxicated mice, next, we investigated if functional blocking antibodies against RANTES and eotaxin protected the nigrostriatum from MPTP insult. Mice were treated once with functional blocking antibodies against RANTES and eotaxin 2 h after the last injection of MPTP and seven days after the last injection of MPTP, status of nigral TH neurons and striatal TH fibers were monitored. MPTP-intoxication led to approximately 65% loss of SNpc TH-positive neurons (FIG. 9A-B) compared with saline-injected controls. However, in MPTP-injected mice treated with functional blocking antibodies against RANTES and eotaxin, the reduction in SNpc TH-positive neurons was about 22% (FIG. 9A-B). On the other hand, no such protective effects were seen in MPTP-intoxicated mice that were treated with control IgG (FIG. 9A-B). Results were also corroborated by TH Western blot data of nigral homogenates (FIG. 9C-D). Similar to the loss of nigral TH neurons, MPTP-intoxication led to approximately 68% reduction of striatal TH ODs (FIG. 10A-B) compared with saline-injected controls. Again, marked protection of striatal TH fibers was noted in MPTP-injected mice treated with neutralizing antibodies against RANTES and eotaxin (FIG. 10A-B). To determine whether neutralization of RANTES and eotaxin protects against biochemical deficits caused by MPTP, we quantified the level of DA, DOPAC and HVA in the striata 7 days after the MPTP treatment. MPTP intoxication led to marked decrease in striatal DA (FIG. 10C), DOPAC (FIG. 10D) and HVA (FIG. 10E) compared to striata of saline-injected mice. In contrast, MPTP-intoxicated animals that received one injection of neutralizing antibodies against RANTES and eotaxin showed only 10-20% loss in striatal DA, DOPAC and HVA (FIG. 10C-E). On the other hand, such protection was not seen in case of control IgG treatment (FIG. 10C-E). Functional blocking antibodies against RANTES and eotaxin improve locomotor functions in MPTP-intoxicated mice: The ultimate therapeutic goal of neuroprotection in PD is to decrease functional impairment.

Figure 11:
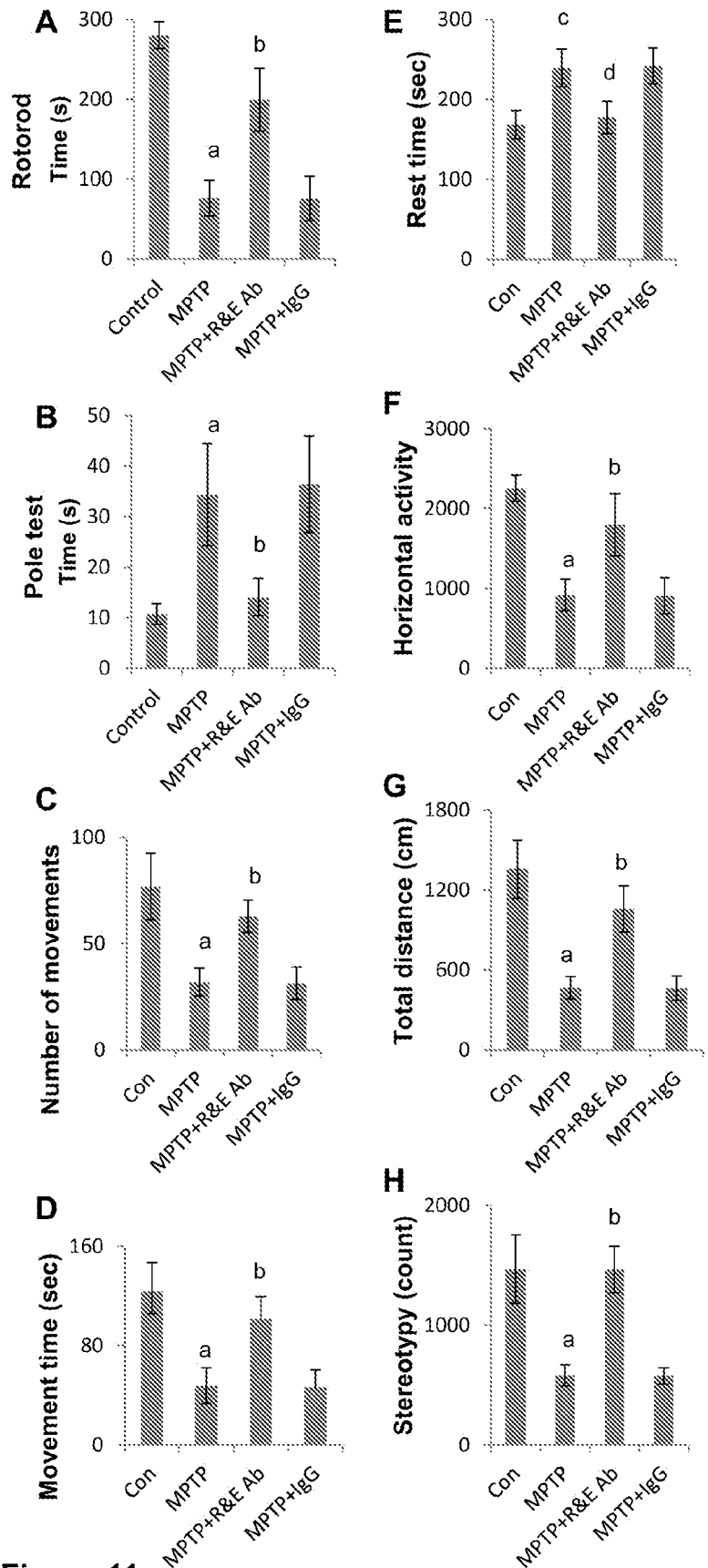
FIG. 11A-11H. Neutralization of RANTES and eotaxin improves motor functions in MPTP-intoxicated mice. Male C57/BL6 mice (6-8 week old) were insulted with 20 mg/kg body wt MPTP (four injections at every 2 h interval). After 2 h of the last injection of MPTP, animals were treated with the combination of 20 μg/mouse anti-RANTES Ab and 20 μg/mouse antieotaxin Ab via i.p. injection. After 7 d of the last injection of MPTP, mice were tested for motor functions (FIG. 11A, rotorod.

Therefore, to examine whether neutralization of RANTES and eotaxin protects not only against structural and neurotransmitter damage but also against functional impairments caused by MPTP, we monitored bradykinesia by pole test and locomotor functions by rotorod and open-field activities. MPTP insult caused a marked decrease in rotorod performance (FIG. 11A), pole test (FIG. 11B), number of movements (FIG. 11C), movement time (FIG. 11D), horizontal activity (FIG. 11F), total distance (FIG. 11G), and stereotypy (FIG. 11H). On the other hand, MPTP insult increased the rest time (FIG. 11E). However, neutralizing antibodies against RANTES and eotaxin significantly improved MPTP-induced hypolocomotion and bradykinesia (FIG. 11A-H).

DISCUSSION

PD is a progressive age-related neurodegenerative disease with unclear etiology. This disease sometimes progresses ruthlessly, leaving its victims bound to the wheelchair or dependent on caregivers. Despite intense investigations effective therapy against PD is still unavailable. Administration of a dopamine agonist or levodopa has been the standard treatment for PD. However, it is often associated with a number of side effects and unsatisfactory outcomes. Therefore, understanding the mechanism of the disease process of PD and development of effective neuroprotective therapeutic approach to halt the disease progression are of paramount importance. Here, we have seen rapid increase in RANTES and eotaxin in the nigra and serum of mice upon MPTP intoxication. Although microglia were main producers of RANTES and eotaxin in the SNpc of MPTP-intoxicated mice, we also noticed some RANTES and eotaxin in GFAP-positive astrocytes. Furthermore, increase in RANTES and eotaxin in the SNpc of postmortem PD brains as compared to age-matched controls suggest that these chemokines may play a role in the loss of nigral dopaminergic neurons in PD. Since the increase in RANTES and eotaxin was also seen in serum of MPTP-intoxicated mice, we used functional blocking antibodies to neutralize their activities in the periphery. Several lines of evidence clearly suggest that peripheral administration of functional blocking antibodies against RANTES and eotaxin reduces inflammation and protects the nigrostriatum in MPTP-intoxicated mice. Our conclusion is based on the following: First, inflammation plays a role in the pathogenesis of nigrostriatal degeneration in PD patients and MPTP-intoxicated mice (12, 17, 18, 32, 33). Accordingly, MPTP insult increased the expression of different proinflammatory cytokines (TNFα, IL-1β and IL-6) and iNOS in the SNpc. However, i.p. injection of a combination of antibodies against RANTES and eotaxin markedly decreased the expression of these proinflammatory molecules in the SNpc of MPTP-intoxicated mice. Second, as expected, MPTP intoxication led to glial activation in the nigra as evident by marked increase in expression of GFAP and CD11b, which was inhibited by treatment of antibodies against RANTES and eotaxin. Third, as observed in PD, nigral dopaminergic neurons disappeared in MPTP-intoxicated mice. But treatment with antibodies against RANTES and eotaxin protected TH-positive dopaminergic neurons from MPTP toxicity. Fourth, treatment with antibodies against RANTES and eotaxin also protected striatal TH fibers from MPTP toxicity and restored the level of neurotransmitters. Lastly, antibody treatment ameliorated functional impairment in MPTP-intoxicated mice. We did not notice any side effect (e.g. hair loss, weight loss, untoward infection etc.) in any of the mice used during the course of the study, suggesting that antibodies against RANTES and eotaxin may not exhibit any side effects. RANTES (34) and eotaxin (35) are two important proinflammatory chemokines that are produced by T cells and antigen-presenting cells such as macrophages and microglia. RANTES, a 68 amino acid-long polypeptide, is known to induce the migration and homing of classical lymphoid cells such as T cells and monocytes, and other immune cells including basophils, eosinophils, natural killer cells, dendritic cells, and mast cells (36). Similarly, eotaxin, another small 71 amino acid-long chemokine, is capable of inducing infiltration of mononuclear cells in the site of inflammation (37). Therefore, major function of these two chemokines is to control the homing of T cells. Earlier few studies have already reported infiltration of T cells into the nigra of MPTP mouse model (5) and MPTP-intoxicated rhesus monkeys (7). Here, we have also seen marked infiltration of CD4+ and relatively less infiltration of CD8+ T cells into the nigra upon MPTP intoxication. Interestingly, neutralization of RANTES and eotaxin strongly inhibited the infiltration of both CD4+ and CD8+ T cells into the nigra of MPTP-intoxicated mice, suggesting that MPTP insult induces infiltration of T cells into the nigra via RANTES and eotaxin.

Although whether T cell infiltration is primary or secondary to nigrostriatal degeneration is still unclear, once T cells infiltrate into the nigra, there are several direct and indirect pathways by which T cells could influence dopaminergic neurodegeneration. For example, it has been reported that the migration of antigen-specific CD4+ T cells from the periphery to the CNS generates immunocyte-microglial activities that perpetuate neuroinflammation and affect neuronal survival (38). Earlier we have shown that effector T cells are capable of activating microglia for the production of various proinflammatory molecules via cell-to-cell contact (19, 39). This contact process involves VLA4 ($\alpha 4\beta 1$) integrin of T cells and VCAM1 of microglia (19, 40). Furthermore, activated T cells may also activate microglia via CD40-CD40 ligation (41-43). According to Nitsch et al (44), cytotoxic T cell-mediated lethal increase in neuronal calcium could be prevented by blocking both perforin and glutamate receptors.

In summary, we have demonstrated that MPTP intoxication leads to rapid increase in RANTES and eotaxin in the SNpc and serum of mice and that neutralization of these two chemokines protect nigral dopaminergic neurons. Although MPTP mouse model does not recapitulate all the features of PD in humans, RANTES and eotaxin are also upregulated in the nigra of postmortem PD brains as compared to control brains. Therefore, our results suggest that neutralizing antibodies against RANTES and eotaxin may have therapeutic efficacy in PD.

Materials and Methods

Reagents: Mouse RANTES and eotaxin ELISA kits were purchased from R&D Systems (Minneapolis, Minn.). Anti-CD3, CD4 and CD8 antibodies were purchased from eBioscience. Rabbit anti-TH antibody was purchased from Millipore. Anti-Iba-1 antibody was purchased from Abcam.

Cy2- and Cy5-conjugated antibodies were obtained from Jackson Immuno Research Laboratories (West Grove, Pa.).

Animals and MPTP intoxication: Six- to eight-week old C57BL/6 mice were purchased from Harlan, Indianapolis, Ind. Animal maintenance and experiments were in accordance with National Institutes of Health guidelines and were approved by the Institutional Animal Care and Use committee of the Rush University Medical Center, Chicago, Ill. For acute MPTP intoxication, mice received four intraperitoneal (i.p.) injections of MPTP-HCl (1-methyl-4-phenyl-1,2,3,6-tetrahydropyridine) (18 mg/kg of free base; Sigma Chemical Co., St. Louis, Mo.) in saline at 2-h intervals (12, 17, 18, 22, 23). Control animals received only saline.

Human Brain Tissue: Autopsy brain tissues from four male PD patients and four control subjects were obtained from the Rush PD Center Brain Bank. PD patients and control subjects did not differ significantly for their mean age at death (PD, 74±3 years; control, 79±18 years). The mean postmortem interval for PD and controls were 4.1±0.8 and 10.9±1.1 h, respectively.

Treatment of MPTP-intoxicated mice with neutralizing antibodies against RANTES and eotaxin: Azide-free neutralizing antibodies against RANTES/CCL5 and eotaxin/CCL11 were obtained from R&D Systems (Minneapolis, Minn.). After 2 h of the last injection of MPTP, mice were treated once with the combination of anti-RANTES Ab (20 µg/mouse) and anti-eotaxin Ab (20 µg/mouse) via i.p. injection. Antibodies were reconstituted in sterile PBS such a way that total injection volume remained at 100 µl per mouse. A group of MPTP intoxicated mice also received IgG (40 µg/mouse) as control via i.p. injection.

Semi-quantitative RT-PCR analysis: Total RNA was isolated from nigra using Ultraspec-II RNA reagent (Biotecx Laboratories, Inc., Houston, Tex.) following the manufacturer's protocol. To remove any contaminating genomic DNA, total RNA was digested with DNase. RT-PCR was carried out as described earlier (17, 24, 25) using a RT-PCR kit (Clontech, Mountain View, Calif.) and following primers:

```
iNOS:
Sense:
                                            (SEQ ID NO 1)
5'-CCCTTCCGAAGTTTCTGGCAGCAGC-3'

Antisense:
                                            (SEQ ID NO 2)
5'-GGCTGTCAGAGCCTCGTGGCTTTGG-3'

IL-1β:
Sense:
                                            (SEQ ID NO 3)
5'-CTCCATGAGCTTTGTACAAGG-3'

Antisense:
                                            (SEQ ID NO 4)
5'-TGCTGATGTACCAGTTGGGG-3'

IL-6:
Sense:
                                            (SEQ ID NO 5)
5'-GACAACTTTGGCATTGTGG-3'

Antisense:
                                            (SEQ ID NO 6)
5'-ATGCAGGGATGATGTICTG-3'

TNFα:
Sense:
                                            (SEQ ID NO 7)
5'-TTCTGTCTACTGAACTTCGGGGTGATCGGTCC-3'

Antisense:
                                            (SEQ ID NO 8)
5'-GTATGAGATAGCAAATCGGCTGACGGTGTGGG-3'

RANTES:
Sense:
                                            (SEQ ID NO 9)
5'-ATACGCTICCCTGICATCGC-3'

Antisense:
                                            (SEQ ID NO 10)
5'-TTGGGTTTCGTGGTCGAGAG-3'

Eotaxin:
Sense:
                                            (SEQ ID NO 11)
5'-AGCTAGTCGGGAGAGCCTAC-3'

Antisense:
                                            (SEQ ID NO 12)
5'-AAGGAAGTGACCGTGAGCAG-3'

CD11b:
Sense:
                                            (SEQ ID NO 13)
5'-GTGAGGATTCCTACGGGACCCAGGT -3'

Antisense:
                                            (SEQ ID NO 14)
5'-GGCGTACTTCACAGGCAGCTCCAAC-3'

GFAP:
Sense:
                                            (SEQ ID NO 15)
5'-GGCGCTCAATGCTGGCTTCA-3'

Antisense:
                                            (SEQ ID NO 16)
5'-TCTGCCTCCAGCCTCAGGTT-3'

GAPDH:
Sense:
                                            (SEQ ID NO 17)
5'-GGTGAAGGTCGGTGTGAACG-3'

Antisense:
                                            (SEQ ID NO 18)
5'-TTGGCTCCACCCTICAAGTG-3'
```

Real-time PCR analysis: DNase-digested RNA was analyzed by real-time PCR in the ABI-Prism7700 sequence detection system (Applied Biosystems, Foster City, Calif.) as described earlier (17, 24-26) using TaqMan Universal Master mix and optimized concentrations of FAM-labeled probes and primers. Data were processed using the ABI Sequence Detection System 1.6 software.

Western blot Analysis: Immunoblot analysis for RANTES, eotaxin, iNOS, IL-1β, GFAP, Iba-1, and TH was carried out as described earlier (26-28). Briefly, cell homogenates were electrophoresed, proteins were transferred onto a nitrocellulose membrane, and bands were visualized with an Odyssey infrared scanner after immunolabeling with respective primary antibodies followed by infra-red fluorophore-tagged secondary antibody (Invitrogen).

Immunohistochemistry and quantitative morphology: Seven days after MPTP intoxication, mice were sacrificed and their brains fixed, embedded, sectioned (30 µm thick), and processed for tyrosine hydroxylase (TH) and thionin staining as described previously (18, 30). Total numbers of TH- and Nissl-stained neurons in SNpc were counted stereologically with STEREO INVESTIGATOR software (MicroBrightfield, Williston, Vt.) by using an optical fractionator (18, 30). Quantitation of striatal TH immunostaining was performed as described (18, 30). Optical density measurements were obtained by digital image analysis (Scion, Frederick, Md.). Striatal TH optical density reflected dopaminergic fiber innervation. For immunofluorescence staining on fresh frozen nigral sections isolated from mice after 1 d of MPTP insult, goat anti-mouse RANTES (1:100), rat anti-mouse eotaxin (1:100), rabbit anti-mouse Iba1 (1:100), goat anti-mouse GFAP (1:100), mouse anti-mouse CD4 (1:100), and mouse anti-mouse iNOS (1:250) were used. The samples were mounted and observed under a Bio-Rad MRC1024ES confocal laser scanning microscope.

HPLC analysis for measurement of striatal Dopamine and its metabolite levels: Striatal level of dopamine, DOPAC (3, 4-dihydroxyphenylacetic acid) and HVA (homovanillic acid) was quantified as described earlier (10, 12, 18, 22, 30). Briefly, mice were sacrificed by cervical dislocation after 7 days of MPTP intoxication and their striata were collected and immediately frozen in dry ice and stored at −80 C until analysis. On the day of the analysis, tissues were sonicated in 0.2M perchloric acid containing isoproterenol and resulting homogenates were centrifuged at 20,000×g for 15 min at 4 C. After pH adjustment and filtration, 10 µl 10 µl of supernatant was injected onto a Eicompak SC-3ODS column (Complete Stand-Alone HPLCECDHPLC-ECD System EiCOMHTEC-500 from JM Science Inc., Grand Island, N.Y.) and analyzed following manufacturer's protocol.

Behavioral analyses: Three types of behavioral experiments were conducted. These included an open field experiment for locomotor activity, a pole test for bradykinesia and a rotorod experiment for feet movement as described earlier (12, 17, 18, 22, 31). Locomotor activity was measured after 7 d of the last dose of MPTP injection in a Digiscan Monitor (Omnitech Electronics, Inc., Columbus, Ohio). This Digiscan Monitor records stereotypy and rearing, behaviors that are directly controlled by striatum, as well as other basic locomotion parameters, such as horizontal activity, total distance traveled, number of movements, movement time, rest time, mean distance mean time, and center time. Before any insult or treatment, mice were placed inside the Digiscan Infra-red Activity Monitor for 10 min daily and on rotorod for 10 min daily for 3 consecutive days to train them and record their baseline values. Briefly, animals were removed directly from their cages and gently placed nose first into a specified corner of the open-field apparatus and after release, data acquisition began at every 5 min interval. DIGISCAN software was used to analyze and store horizontal and vertical activity data, which were monitored automatically by infra-red beams. Bradykinesia was measured by the time to turn head-down and completely descend a wooden pole wrapped in cloth tape. Briefly, mice were acclimatized to the pole (1 cm diameter, 40 cm height) over 3 trials of 120 s each. Each trial was separated by 60 s and during behavioral testing, each mouse was tested thrice. In rotorod, the feet movement of the mice was observed at different speeds. To eliminate stress and fatigues, mice were given a 5-min rest interval.

Statistical analysis: All values are expressed as means±SEM. Differences among means were analyzed by one-way ANOVA or Kruskal-Wallis test (comparison among all four groups) and post-hoc pair-wise comparison. In other cases, two sample t tests were also used to compare control vs MPTP and MPTP vs antibody.

EQUIVALENTS

The foregoing written specification is considered to be sufficient to enable one skilled in the art to practice the invention. The foregoing description and examples detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

REFERENCES

1. Vila, M., and Przedborski, S. (2004) Genetic clues to the pathogenesis of Parkinson's disease. *Nat Med* 10 Suppl, S58-62
2. Olanow, C. W., and Tatton, W. G. (1999) Etiology and pathogenesis of Parkinson's disease. *Annu Rev Neurosci* 22, 123-144
3. Dauer, W., and Przedborski, S. (2003) Parkinson's disease: mechanisms and models. *Neuron* 39, 889-909
4. Martin, H. L., Santoro, M., Mustafa, S., Riedel, G., Forrester, J. V., and Teismann, P. (2015) Evidence for a role of adaptive immune response in the disease pathogenesis of the MPTP mouse model of Parkinson's disease. *Glia*
5. Brochard, V., Combadiere, B., Prigent, A., Laouar, Y., Perrin, A., Beray-Berthat, V., Bonduelle, O., Alvarez-Fischer, D., Callebert, J., Launay, J. M., Duyckaerts, C., Flavell, R. A., Hirsch, E. C., and Hunot, S. (2009) Infiltration of CD4+ lymphocytes into the brain contributes to neurodegeneration in a mouse model of Parkinson disease. *J Clin Invest* 119, 182-192
6. Reynolds, A. D., Stone, D. K., Hutter, J. A., Benner, E. J., Mosley, R. L., and Gendelman, H. E. (2010) Regulatory T cells attenuate Th17 cell-mediated nigrostriatal dopaminergic neurodegeneration in a model of Parkinson's disease. *J Immunol* 184, 2261-2271
7. Roy, A., Mondal, S., Kordower, J. H., and Pahan, K. (2015) Attenuation of microglial RANTES by NEMO-binding domain peptide inhibits the infiltration of CD8(+) T cells in the nigra of hemiparkinsonian monkey. *Neuroscience* 302, 36-46
8. Benner, E. J., Banerjee, R., Reynolds, A. D., Sherman, S., Pisarev, V. M., Tsiperson, V., Nemachek, C., Ciborowski, P., Przedborski, S., Mosley, R. L., and Gendelman, H. E. (2008) Nitrated alpha-synuclein immunity accelerates degeneration of nigral dopaminergic neurons. *PLoS One* 3, e1376
9. Lee, J. K., Chung, J., McAlpine, F. E., and Tansey, M. G. (2011) Regulator of G-protein signaling-10 negatively regulates NF-kappaB in microglia and neuroprotects dopaminergic neurons in hemiparkinsonian rats. *J Neurosci* 31, 11879-11888
10. Roy, A., Fung, Y. K., Liu, X., and Pahan, K. (2006) Up-regulation of microglial CD11b expression by nitric oxide. *J Biol Chem* 281, 14971-14980
11. Roy, A., Jana, A., Yatish, K., Freidt, M. B., Fung, Y. K., Martinson, J. A., and Pahan, K. (2008) Reactive oxygen species up-regulate CD11b in microglia via nitric oxide: Implications for neurodegenerative diseases. *Free Radic Biol Med* 45, 686-699
12. Khasnavis, S., Roy, A., Ghosh, S., Watson, R., and Pahan, K. (2014) Protection of dopaminergic neurons in a mouse model of Parkinson's disease by a physically-modified saline containing charge-stabilized nanobubbles. *J Neuroimmune Pharmacol* 9, 218-232
13. Perry, V. H., Cunningham, C., and Holmes, C. (2007) Systemic infections and inflammation affect chronic neurodegeneration. *Nat Rev Immunol* 7, 161-167
14. Cunningham, C., Campion, S., Lunnon, K., Murray, C. L., Woods, J. F., Deacon, R. M., Rawlins, J. N., and Perry, V. H. (2009) Systemic inflammation induces acute behavioral and cognitive changes and accelerates neurodegenerative disease. *Biol Psychiatry* 65, 304-312

15. Field, R., Campion, S., Warren, C., Murray, C., and Cunningham, C. (2010) Systemic challenge with the TLR3 agonist poly I:C induces amplified IFNalpha/beta and IL-1 beta responses in the diseased brain and exacerbates chronic neurodegeneration. *Brain Behav Immun* 24, 996-1007

16. Pahan, P., and Pahan, K. (2015) Can cinnamon bring aroma in Parkinson's disease treatment? *Neural Regen Res* 10, 30-32

17. Ghosh, A., Roy, A., Matras, J., Brahmachari, S., Gendelman, H. E., and Pahan, K. (2009) Simvastatin inhibits the activation of p21ras and prevents the loss of dopaminergic neurons in a mouse model of Parkinson's disease. *J Neurosci* 29, 13543-13556

18. Ghosh, A., Roy, A., Liu, X., Kordower, J. H., Mufson, E. J., Hartley, D. M., Ghosh, S., Mosley, R. L., Gendelman, H. E., and Pahan, K. (2007) Selective inhibition of NF-kappaB activation prevents dopaminergic neuronal loss in a mouse model of Parkinson's disease. *Proc Natl Acad Sci USA* 104, 18754-18759

19. Dasgupta, S., Jana, M., Liu, X., and Pahan, K. (2003) Role of very-late antigen-4 (VLA-4) in myelin basic protein-primed T cell contact-induced expression of proinflammatory cytokines in microglial cells. *J Biol Chem* 278, 22424-22431

20. Dasgupta, S., Jana, M., Liu, X., and Pahan, K. (2005) Myelin basic protein-primed T cells of female but not male mice induce nitric-oxide synthase and proinflammatory cytokines in microglia: implications for gender bias in multiple sclerosis. *J Biol Chem* 280, 32609-32617

21. Dasgupta, S., Roy, A., Jana, M., Hartley, D. M., and Pahan, K. (2007) Gemfibrozil ameliorates relapsing-remitting experimental autoimmune encephalomyelitis independent of peroxisome proliferator-activated receptor-alpha. *Mol Pharmacol* 72, 934-946

22. Khasnavis, S., and Pahan, K. (2014) Cinnamon treatment upregulates neuroprotective proteins Parkin and DJ-1 and protects dopaminergic neurons in a mouse model of Parkinson's disease. *J Neuroimmune Pharmacol* 9, 569-581

23. Roy, A., Ghosh, A., Jana, A., Liu, X., Brahmachari, S., Gendelman, H. E., and Pahan, K. (2012) Sodium phenylbutyrate controls neuroinflammatory and antioxidant activities and protects dopaminergic neurons in mouse models of Parkinson's disease. *PLoS One* 7, e38113

24. Jana, M., Jana, A., Liu, X., Ghosh, S., and Pahan, K. (2007) Involvement of phosphatidylinositol 3-kinase-mediated up-regulation of I kappa B alpha in anti-inflammatory effect of gemfibrozil in microglia. *J Immunol* 179, 4142-4152

25. Brahmachari, S., Jana, A., and Pahan, K. (2009) Sodium benzoate, a metabolite of cinnamon and a food additive, reduces microglial and astroglial inflammatory responses. *J Immunol* 183, 5917-5927

26. Khasnavis, S., and Pahan, K. (2012) Sodium Benzoate, a Metabolite of Cinnamon and a Food Additive, Upregulates Neuroprotective Parkinson Disease Protein DJ-1 in Astrocytes and Neurons. *J Neuroimmune Pharmacol*

27. Saha, R. N., Liu, X., and Pahan, K. (2006) Up-regulation of BDNF in astrocytes by TNF-alpha: a case for the neuroprotective role of cytokine. *J Neuroimmune Pharmacol* 1, 212-222

28. Roy, A., Jana, M., Corbett, G. T., Ramaswamy, S., Kordower, J. H., Gonzalez, F. J., and Pahan, K. (2013) Regulation of cyclic AMP response element binding and hippocampal plasticity-related genes by peroxisome proliferator-activated receptor alpha. *Cell Rep* 4, 724-737

29. Roy, A., Jana, M., Kundu, M., Corbett, G. T., Rangaswamy, S. B., Mishra, R. K., Luan, C. H., Gonzalez, F. J., and Pahan, K. (2015) HMG-CoA Reductase Inhibitors Bind to PPARalpha to Upregulate Neurotrophin Expression in the Brain and Improve Memory in Mice. *Cell Metab* 22, 253-265

30. Benner, E. J., Mosley, R. L., Destache, C. J., Lewis, T. B., Jackson-Lewis, V., Gorantla, S., Nemachek, C., Green, S. R., Przedborski, S., and Gendelman, H. E. (2004) Therapeutic immunization protects dopaminergic neurons in a mouse model of Parkinson's disease. *Proceedings of the National Academy of Sciences of the United States of America* 101, 9435-9440

31. Roy, A., and Pahan, K. Prospects of statins in Parkinson disease. *Neuroscientist* 17, 244-255

32. Wu, D. C., Jackson-Lewis, V., Vila, M., Tieu, K., Teismann, P., Vadseth, C., Choi, D. K., Ischiropoulos, H., and Przedborski, S. (2002) Blockade of microglial activation is neuroprotective in the 1-methyl-4-phenyl-1,2,3,6-tetrahydropyridine mouse model of Parkinson disease. *J Neurosci* 22, 1763-1771

33. Mondal, S., Roy, A., Jana, A., Ghosh, S., Kordower, J. H., and Pahan, K. (2012) Testing NF-kappaB-based therapy in hemiparkinsonian monkeys. *J Neuroimmune Pharmacol* 7, 544-556

34. Hu, S., Chao, C. C., Ehrlich, L. C., Sheng, W. S., Sutton, R. L., Rockswold, G. L., and Peterson, P. K. (1999) Inhibition of microglial cell RANTES production by IL-10 and TGF-beta. *J Leukoc Biol* 65, 815-821

35. Wei, J., Wu, F., Sun, X., Zeng, X., Liang, J. Y., Zheng, H. Q., Yu, X. B., Zhang, K. X., and Wu, Z. D. (2013) Differences in microglia activation between rats-derived cell and mice-derived cell after stimulating by soluble antigen of IV larva from *Angiostrongylus cantonensis* in vitro. *Parasitol Res* 112, 207-214

36. Appay, V., and Rowland-Jones, S. L. (2001) RANTES: a versatile and controversial chemokine. *Trends Immunol* 22, 83-87

37. Wada, T., Furuichi, K., Sakai, N., Shimizu, M., Segawa, C., Kobayashi, K., Mukaida, N., Kasahara, T., Matsushima, K., and Yokoyama, H. (1999) Eotaxin contributes to renal interstitial eosinophilia. *Nephrol Dial Transplant* 14, 76-80

38. Gendelman, H. E., and Mosley, R. L. (2015) A Perspective on Roles Played by Innate and Adaptive Immunity in the Pathobiology of Neurodegenerative Disorders. *J Neuroimmune Pharmacol* 10, 645-650

39. Dasgupta, S., Jana, M., Liu, X., and Pahan, K. (2002) Myelin basic protein-primed T cells induce nitric oxide synthase in microglial cells. Implications for multiple sclerosis. *J Biol Chem* 277, 39327-39333

40. Brahmachari, S., and Pahan, K. (2010) Gender-specific expression of beta1 integrin of VLA-4 in myelin basic protein-primed T cells: implications for gender bias in multiple sclerosis. *J Immunol* 184, 6103-6113

41. Jana, M., Dasgupta, S., Liu, X., and Pahan, K. (2002) Regulation of tumor necrosis factor-alpha expression by CD40 ligation in BV-2 microglial cells. *J Neurochem* 80, 197-206

42. Jana, M., Liu, X., Koka, S., Ghosh, S., Petro, T. M., and Pahan, K. (2001) Ligation of CD40 stimulates the induction of nitric-oxide synthase in microglial cells. *J Biol Chem* 276, 44527-44533

43. Chabot, S., Charlet, D., Wilson, T. L., and Yong, V. W. (2001) Cytokine production consequent to T cell-microglia interaction: the PMA/IFN gamma-treated U937 cells display similarities to human microglia. *J Neurosci Methods* 105, 111-120

44. Nitsch, R., Pohl, E. E., Smorodchenko, A., Infante-Duarte, C., Aktas, O., and Zipp, F. (2004) Direct impact of T cells on neurons revealed by two-photon microscopy in living brain tissue. *J Neurosci* 24, 2458-2464

The invention claimed is:

1. A method of treating Parkinson's disease in a subject, the method comprising:
    administering a composition to the subject in need thereof to treat Parkinson's disease, the composition comprising a neutralizing antibody to RANTES and a neutralizing antibody to eotaxin.

2. The method of claim 1, comprising administering the composition in a single administration.

3. The method of claim 1, comprising administering the composition by injection.

* * * * *

UNITED STATES PATENT AND TRADEMARK OFFICE
CERTIFICATE OF CORRECTION

| | | |
|---|---|---|
| PATENT NO. | : 11,034,758 B2 | Page 1 of 1 |
| APPLICATION NO. | : 16/083655 | |
| DATED | : June 15, 2021 | |
| INVENTOR(S) | : Kalipada Pahan | |

It is certified that error appears in the above-identified patent and that said Letters Patent is hereby corrected as shown below:

In the Specification

Column 1, Line 12, insert the following paragraph and paragraph heading:
--STATEMENT AS TO RIGHTS TO INVENTIONS MADE UNDER FEDERALLY SPONSORED RESEARCH AND DEVELOPMENT
This invention was made with government support under NS083054 awarded by the National Institutes of Health. The government has certain rights in the invention.--

Signed and Sealed this
Third Day of September, 2024

*Katherine Kelly Vidal*

Katherine Kelly Vidal
*Director of the United States Patent and Trademark Office*